(12) United States Patent
Militzer et al.

(10) Patent No.: US 10,301,289 B2
(45) Date of Patent: May 28, 2019

(54) METHOD FOR THE PREPARATION OF TRIAZOLE COMPOUNDS

(71) Applicant: BAYER PHARMA AKTIENGESELLSCHAFT, Berlin (DE)

(72) Inventors: Hans-Christian Militzer, Odenthal (DE); Johannes Eggert, Usingen (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 1185 days.

(21) Appl. No.: 14/399,929

(22) PCT Filed: May 6, 2013

(86) PCT No.: PCT/EP2013/059418
§ 371 (c)(1),
(2) Date: Nov. 7, 2014

(87) PCT Pub. No.: WO2013/167552
PCT Pub. Date: Nov. 14, 2013

(65) Prior Publication Data
US 2015/0087827 A1     Mar. 26, 2015

(30) Foreign Application Priority Data
May 8, 2012 (EP) ..................................... 12167152

(51) Int. Cl.
*C07D 403/14* (2006.01)
*C07D 249/04* (2006.01)
*C07D 239/42* (2006.01)

(52) U.S. Cl.
CPC ......... *C07D 403/14* (2013.01); *C07D 239/42* (2013.01); *C07D 249/04* (2013.01)

(58) Field of Classification Search
None
See application file for complete search history.

(56) References Cited

U.S. PATENT DOCUMENTS

| | | | |
|---|---|---|---|
| 4,752,910 A | 6/1988 | Yen et al. | |
| 2005/0154024 A1 | 7/2005 | Bryans et al. | |
| 2010/0305085 A1* | 12/2010 | Thede et al. | C07D 401/14 514/210.2 |

FOREIGN PATENT DOCUMENTS

| | | |
|---|---|---|
| DE | 102008020113 | 10/2009 |
| EP | 0121341 | 10/1984 |
| WO | 2003/101442 A1 | 12/2003 |
| WO | 2004/046120 | 6/2004 |
| WO | 2005/044785 A1 | 5/2005 |
| WO | 2006/114706 | 11/2006 |
| WO | 2006/123242 | 11/2006 |
| WO | 2008/067871 A1 | 6/2008 |
| WO | WO 2009/129945 | 10/2009 |

OTHER PUBLICATIONS

International Search Report (English translation) for International Patent Application No. PCT/EP2013/059418, dated Nov. 14, 2013, 4 pages.
Written Opinion (English translation) for International Patent Application No. PCT/EP2013/059418, dated Nov. 8, 2014, 6 pages.
International Preliminary Report on Patentability for International Patent Application No. PCT/EP2013/059418, dated Nov. 11, 2014, 6 pages.
Fisera, et al., "1,3-Dipolar Cycloadditions to 2,3-Dimethoxycarbonyl-7-Oxabicyclo[2,2,1]-2,5-Heptadiene, 1,4-Epoxy-1,4-Dihydronaphthalene, and exo-endo-1,6-Dimethoxycarbonyl-11,12-Dioxatetracyclo-[4,4,0,12,5,17,10]-3,8-Dodecadiene", Collection of Czech. Chem. Commun. vol. 49, 1984, pp. 1990-2000.
Gold, "Über N-Aminoalkyl-1.2.3-triazole", Liebigs Annalen der Chemie, 205, 1965, pp. 205-216.
Kume, "Orally Active Cephalosporins. II. Synthesis and structure-activity relationships of new 7. Beta.((Z)-2-(2-aminothiazol-4-yl)-2-hydroxyiminoacetamido)-cephalosporins with 1, 2, 3-triazole in C-3 side chain.", Journal of Antibiotics, vol. 46, No. 1, 1993, pp. 177-192.
Postovskii, et al., "New Cases of Tetrazole-Azide Tautomeric Transformations", Polytech. Inst., Sverdlovsk, Doklady Akademii Nauk SSSR, 166(5), 1966, pp. 1136-1139.
Rickborn, "The Retro-Diels-Alder Reaction. Part I. CC Dienophiles", Organic Reactions 52, 1998, pp. 2, 3, 72, 73.
Chesterfield, et al., J. Chem. Soc., 1995, pp. 3478-3481.

* cited by examiner

*Primary Examiner* — Alicia L Otton
(74) *Attorney, Agent, or Firm* — McBee Moore Woodward & Vanik IP, LLC

(57) ABSTRACT

The present invention relates to a process for preparing 1-[6-(morpholin-4-yl)pyrimidin-4-yl]-4-(1H-1,2,3-triazol-1-yl)-1H-pyrazol-5-ol (I—enol form) or 2-[6-(morpholin-4-yl)pyrimidin-4-yl]-4-(1H-1,2,3-triazol-1-yl)-1,2-dihydro-3H-pyrazol-3-one (I—keto form) and sodium 1-[6-(morpholin-4-yl)pyrimidin-4-yl]-4-(1H-1,2,3-triazol-1-yl)-1H-pyrazol-5-olate (II) from 1,2,3-triazole (III), methyl bromoacetate (IV-Me-Br) or ethyl bromoacetate (IV-Et-Br), 4,6-dichloropyrimidine (VIII), morpholine (IX) and hydrazine (XII).

8 Claims, No Drawings

METHOD FOR THE PREPARATION OF TRIAZOLE COMPOUNDS

The present invention relates to a process for preparing 1-[6-(morpholin-4-yl)pyrimidin-4-yl]-4-(1H-1,2,3-triazol-1-yl)-1H-pyrazol-5-ol (I—enol form) or 2-[6-(morpholin-4-yl)pyrimidin-4-yl]-4-(1H-1,2,3-triazol-1-yl)-1,2-dihydro-3H-pyrazol-3-one (I—keto form) and sodium 1-[6-(morpholin-4-yl)pyrimidin-4-yl]-4-(1H-1,2,3-triazol-1-yl)-1H-pyrazol-5-olate (II) from 1,2,3-triazole (III), methyl bromoacetate (IV-Me-Br) or ethyl bromoacetate (IV-Et-Br), 4,6-dichloropyrimidine (VIII), morpholine (IX) and hydrazine (XII).

The compound 1-[6-(morpholin-4-yl)pyrimidin-4-yl]-4-(1H-1,2,3-triazol-1-yl)-1H-pyrazol-5-ol (enol form) or 2-[6-(morpholin-4-yl)pyrimidin-4-yl]-4-(1H-1,2,3-triazol-1-yl)-1,2-dihydro-3H-pyrazol-3-one (keto form) is known from WO 2008/067871 and corresponds to the formula (I)

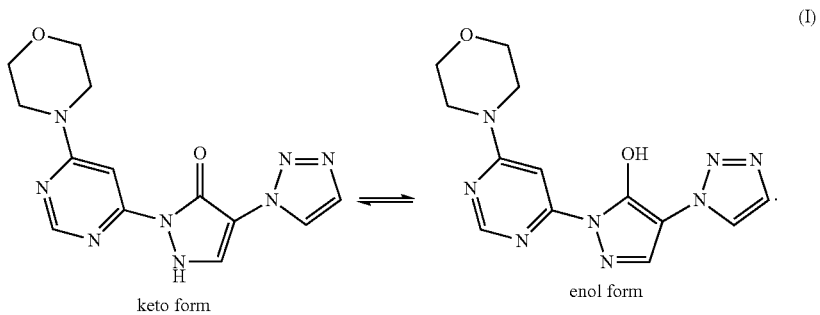 [SMILES: O=c1c(-n2ccnn2)c[nH]n1-c1cc(N2CCOCC2)ncn1 ; Oc1c(-n2ccnn2)cnn1-c1cc(N2CCOCC2)ncn1]

The compound sodium 1-[6-(morpholin-4-yl)pyrimidin-4-yl]-4-(1H-1,2,3-triazol-1-yl)-1H-pyrazol-5-olate corresponds to the formula (II)

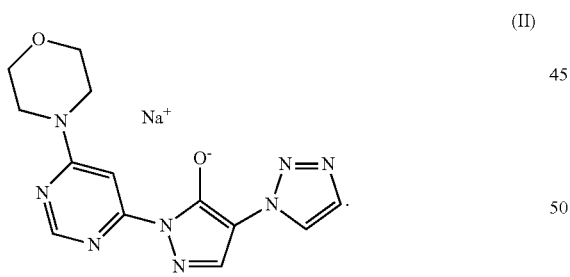

The compounds of the formulae (I) and (II) act as inhibitor for the HIF-prolyl-4-hydroxylases and owing to this specific mechanism of action, lead in vivo after parenteral or oral administration to induction of HIF targeted genes, e.g. erythropoetin, and the biological processes brought about thereby, e.g. erythropoiesis.

WO 2008/067871 describes a synthesis for preparing the compound of the formula (I) in the gramme range from 1,2,3-triazole (III), ethyl bromoacetate (IV-Et-Br), 4,6-dichloropyrimidine (VIII), morpholine (IX) and hydrazine (XII):

Scheme 1
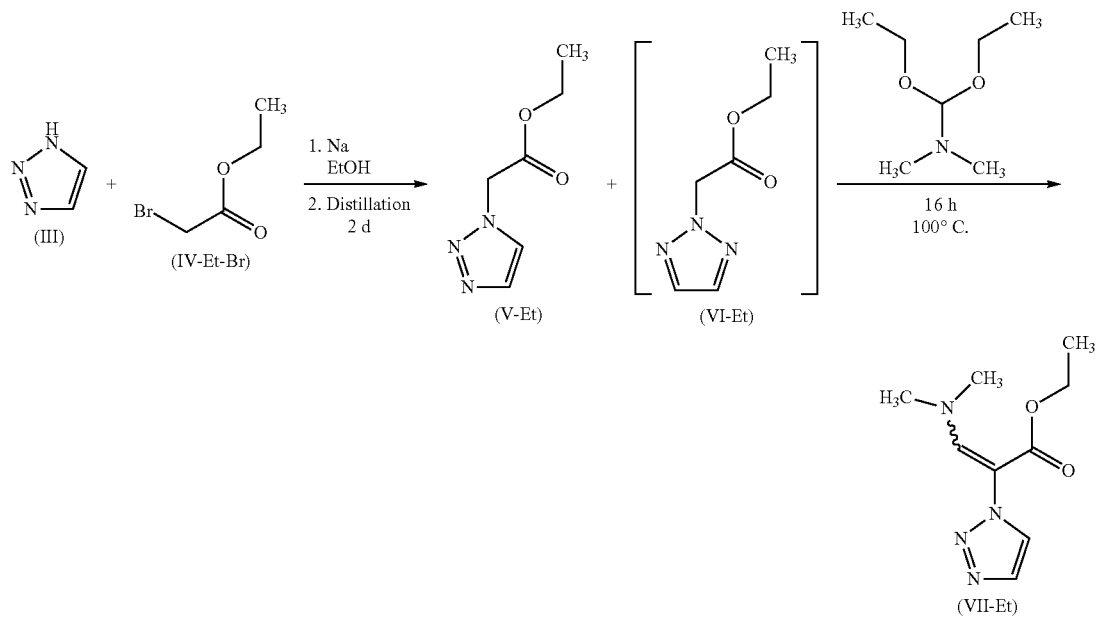
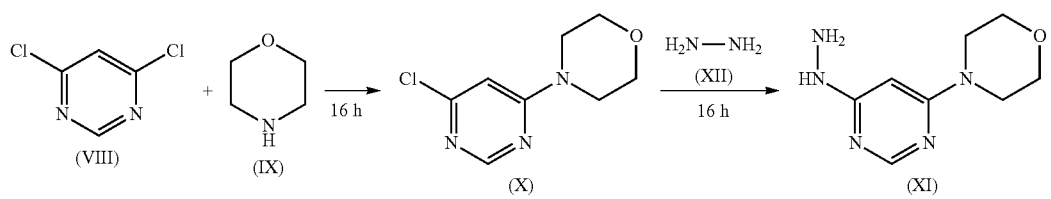
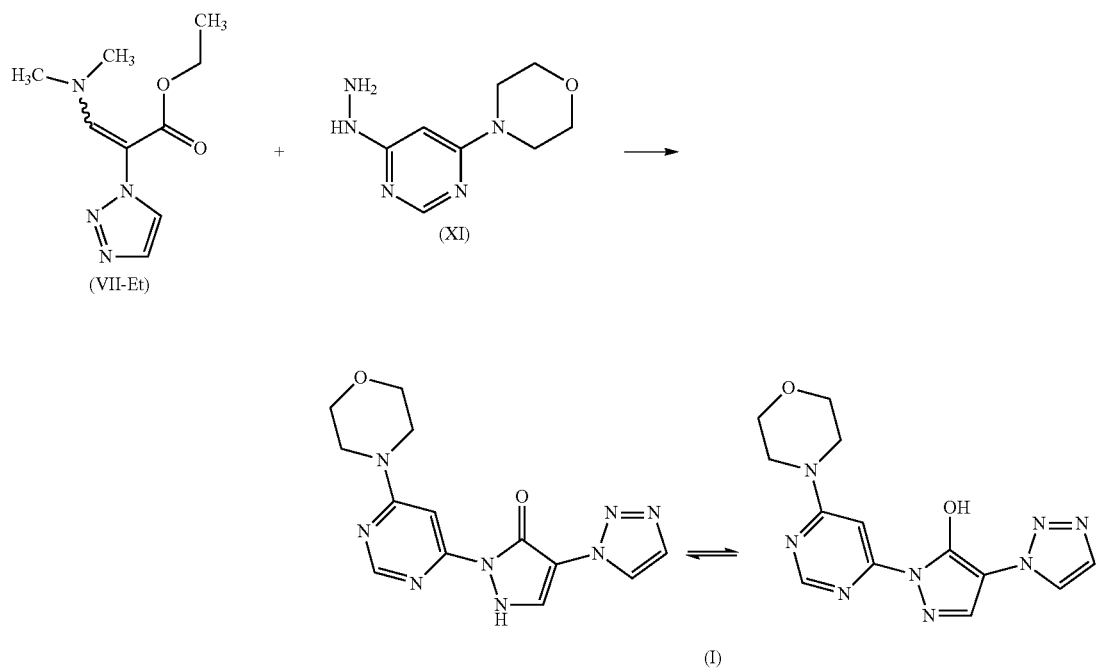

This synthesis of the compound of the formula (I) can be divided into three sections:
a) Preparation of the compound of the formula (VII-Et) from 1,2,3-triazole (III) and ethyl bromoacetate (IV-Et-Br) via the compound of the formula (V-Et).
b) Preparation of the compound of the formula (XI) from 4,6-dichloropyrimidine (VIII), morpholine (IX) and hydrazine (XII).
c) Preparation of the compound of the formula (I) by reaction of the compounds of the formulae (VII-Et) and (XI).

Step a)

For industrial implementation and the production of relatively large kg amounts, the preparative processes described in WO 2008/067871 are suitable to only a limited extent. Thus, in the alkylation of 1,2,3-triazole (III) with ethyl bromoacetate (IV-Et-Br) and sodium ethoxide in ethanol, from about 30 to 40% of the isomeric compound of the formula (VI-Et) are formed in addition to the desired compound of the formula (V-Et). The desired compound of the formula (V-Et) is therefore separated from the isomeric compound of the formula (VI-Et) by vacuum distillation. The low selectivity firstly leads to a low total yield (50%), and secondly the distillation is carried out in a high vacuum and close to the decomposition points of the compounds of the formulae (V-Et) and (VI-Et), and therefore represents a safety risk on the industrial scale. The reaction time of the alkylation of 2 days is very long from a technical point of view since expensive technical plant components are occupied as a result and the costs of the preparation are increased. A lower reaction time of 16 h is likewise required for the preparation of ethyl 3-(dimethylamino)-2-(1H-1,2,3-triazol-1-yl)acrylate (VII-Et). A yield of only 50% is achieved over the two stages. The purification of the compound the formula (VII-Et) can be carried out by chromatography as described in WO 2008/067871 or by stirring with diethyl ether as described in DE 102008020113. Chromatography requires a very high outlay in terms of apparatus on the industrial scale, which is associated with considerable additional costs, and stirring with diethyl ether has been described as bringing about a further loss in yield. Overall, the low selectivity of the alkylation of 1,2,3-triazole (III) with ethyl bromoacetate (IV-Et-Br) represents the critical disadvantage of this process and contributes quite considerably to the low yield of not more than 50%.

It is known that alkylations of 1,2,3-triazole (III) usually proceed with only a low selectivity to the 1-substituted product. According to H. Gold, *Liebigs Annalen der Chemie* (1965) 205 ff, 1,2,3-triazole (III) can be alkylated by means of alkyl halides only with low selectivities. In the respective products, ratios of the 1- and 2-substituted triazoles of from about 3:2 to a maximum of 4:1 are typically obtained. For the alkylation of 1,2,3-triazole (III) by means of ethyl bromoacetate (IV-Et-Br) in the presence of sodium methoxide, a ratio of 3:2 was found (Examples 10 and 11 in H. Gold). Owing to the approximate equivalents of the nitrogen atoms in 1,2,3-triazole (III) a ratio of 2:1 (N-1-isomer to N-2-isomer) would have been expected, and this matches the experimentally determined values very well. Higher proportions of the N-1-isomer desired here were achieved by H. Gold in the alkylation of 1,2,3-triazole (III) using propyl bromide and allyl bromide when triazole was used in excess. However, the conversions achieved are very incomplete, the yields are low and the reaction times are very long.

WO 2006/114706, WO 2006/123242 and US 20050154024 likewise describe the alkylation of 1,2,3-triazole (III) with ethyl bromoacetate (IV-Et-Br). However, only a very low selectivity of 5:6 (N-1-isomer to N-2-isomer) was observed in the procedure using potassium carbonate in ethanol selected there. The same reaction using sodium carbonate as base in acetone as solvent is described by M. Kume, *J. Antibiot.* 46 (1993) 177. After a reaction time of 5 days at 30° C. and purification by means of chromatography, 65% of the compound of the formula (V-Et) and 26% of the compound of the formula (VI-Et) were obtained, which equates to an isomer ratio of 2.5:1.

Ethyl 1H-1,2,3-triazol-1-yl-acetate (V-Et) can, as an alternative, also be prepared by a [3+2]-cycloaddition of acetylene (XIII) and ethyl 2-azidoacetate (XIV-Et), in which only the desired regioisomer of the formula (V-Et) is formed. However, the yield for this reaction is described as being only 11% by L. Fisera and D. Pavlovic, *Collection of Czech. Chem. Commun.* 49 (1984) 1990. A yield of 74% is reported by B. Rickborn, *Organic Reactions* 52 (1998). Acetylene (XIII) and in particular ethyl 2-azidoacetate (XIV-Et) are very high-energy compounds. Organic azides decompose with evolution of nitrogen on supply of only small amounts of energy, e.g. as a result of percussion or an increase in pressure or temperature. They can decompose explosively in such a case. A particularly higher level of safety requirements therefore has to be met for a reaction of acetylene (XIII) with ethyl 2-azidoacetate (XIV-Et) on an industrial scale under superatmospheric pressure and suitable autoclaves are required. These requirements are met by only very few industrial plants.

Scheme 2

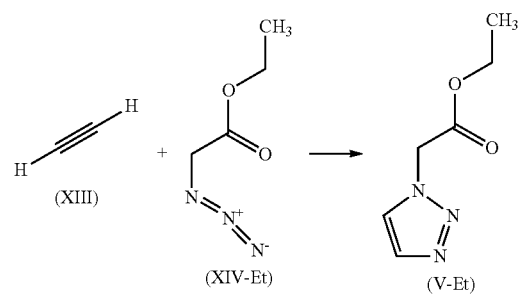

Step b)

In the preparation of 4-(6-hydrazinopyrimidin-4-yl)morpholine (XI) from 4,6-dichloropyrimidine (VIII), morpholine (IX) and 10 molar equivalents of hydrazine hydrate (XII hydrate) as described in WO 2008/067871, a yield of 58% is achieved over two stages after reaction times of in each case 16 hours. The low yield and the long reaction times are unsatisfactory for industrial implementation. The use of the large excess of 10 molar equivalents of hydrazine hydrate (XII hydrate), which is toxic and has been found to cause cancer in test animals, is unsuitable for industrial implementation since it requires complicated wastewater treatment and the product is contaminated by a hydrazine content of above 100 ppm. The same synthetic route to 4-(6-hydrazinopyrimidin-4-yl)morpholine (XI) is selected in WO 2004/046120, although no details of the preparation are given. The same synthetic route is likewise employed in WO 2003/101442, but 3 molar equivalents of hydrazine hydrate (XII hydrate) are reacted in the second reaction step with microwave heating at 120° C. The compound of the formula (XI) is purified by preparative chromatography. Microwave heating is not practicable at present on an industrial scale, and the necessary chromatographic purification would incur additional high costs on an industrial scale.

Scheme 3

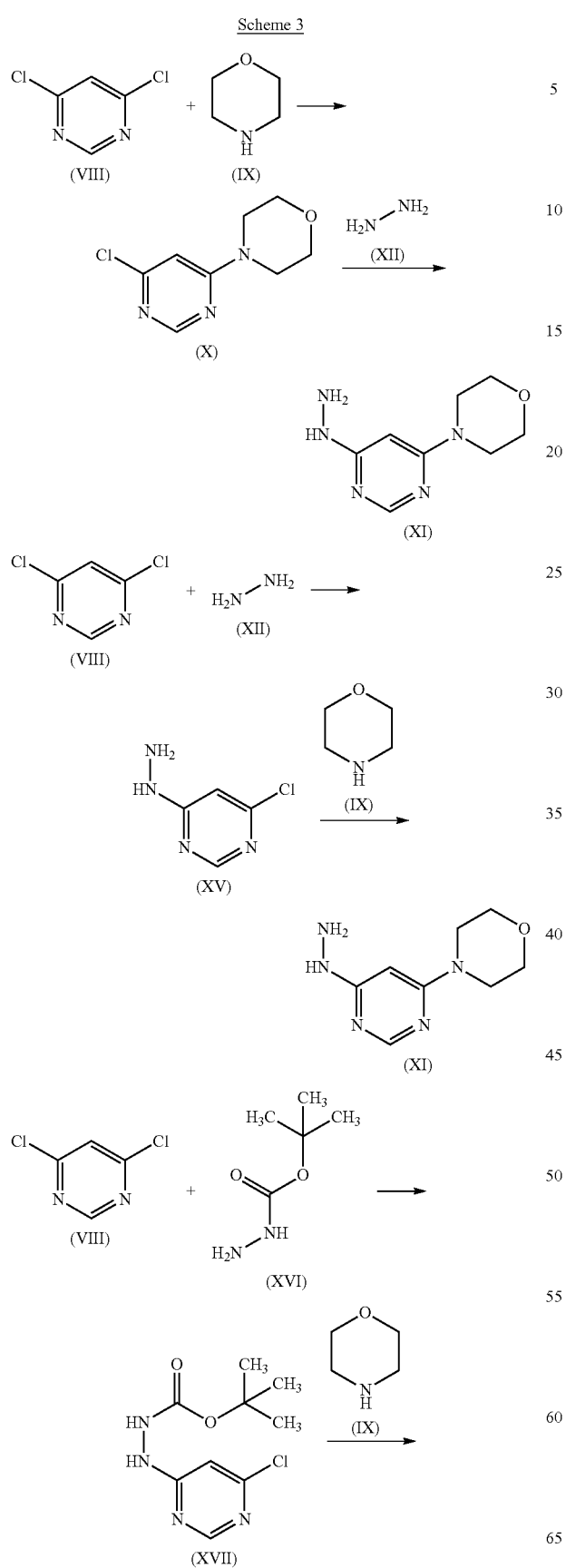
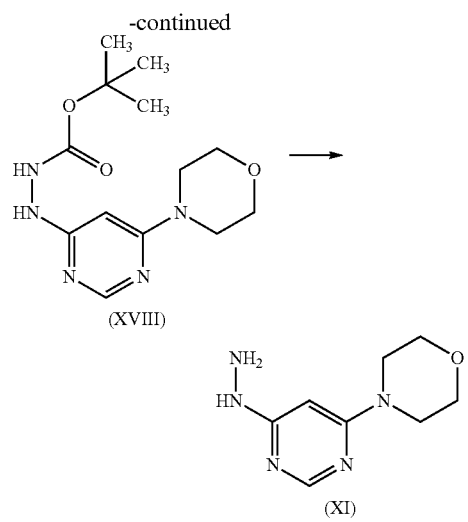

EP 121341 describes the preparation of the compound of the formula (XI) by reaction of the compound of the formula (XV) with 2 molar equivalents of morpholine (IX) in water for 16 h under reflux conditions, subsequent extraction of the compound of the formula (XI) with chloroform and isolation after evaporation of the extract. The extraction with chloroform and also the isolation of the product by evaporation of the extract have only very limited suitability for industrial implementation since chloroform is suspected of being carcinogenic.

Postovskii, Smirnova and Kirov, *Polytech. Inst., Sverdlovsk, Doklady Akademii Nauk SSSR* (1966), 166(5), 1136-9 likewise describe the two-stage preparation of the compound of the formula (XI) via the intermediate of the formula (XV). However, the yield of less than 50% over the two steps which is achieved is unsatisfactory.

Safety studies on the compound of the formula (XV) have shown that this compound is very energy-rich and can be subject to deflagration as a pulverulent solid. The possibility of deflagration represents a safety risk for the handling of this material, especially on an industrial scale, and requires additional technical safety precautions if this material is to be handled in dry form in vessels having movable internals, e.g. drying apparatuses with mechanical stirring, since in the case of friction, e.g. when the stirrer contacts the wall, temperatures sufficient for ignition can arise. However, such apparatuses are preferred for a preparation on the industrial scale since they allow closed handling of even relatively large amounts of dry product through to packaging without employees coming into contact with the product.

WO 2003/101442 describes the preparation of the compound of the formula (XI) via reaction of the compound of the formula (VIII) with tert-butyl carbazate (XVI) at 120° C. with microwave heating to form the intermediate of the formula (XVII). The compound the formula (XVII) is reacted with morpholine (IX) to form a further intermediate of the formula (XVIII) from which the compound of the formula (XI) is subsequently obtained in a total yield of 50% by elimination of the protective group and preparative chromatography. Once again, both microwave heating and the necessary chromatographic purification stand in the way of industrial implementation of this process.

Step c)

The yield of 61% after a reaction time of 16 hours in boiling ethyl acetate and in the presence of trifluoroacetic acid, as described in WO 2008/067871 for the preparation of the compound of the formula (I) from the compounds of the formulae (VII-Et) and (XI), is unsatisfactory for an industrial process. In addition, the product isolated from ethyl acetate contains included salts of trifluoroacetic acid and thus does not meet the requirements in respect of purity demanded of a pharmaceutical active compound.

Scheme 4

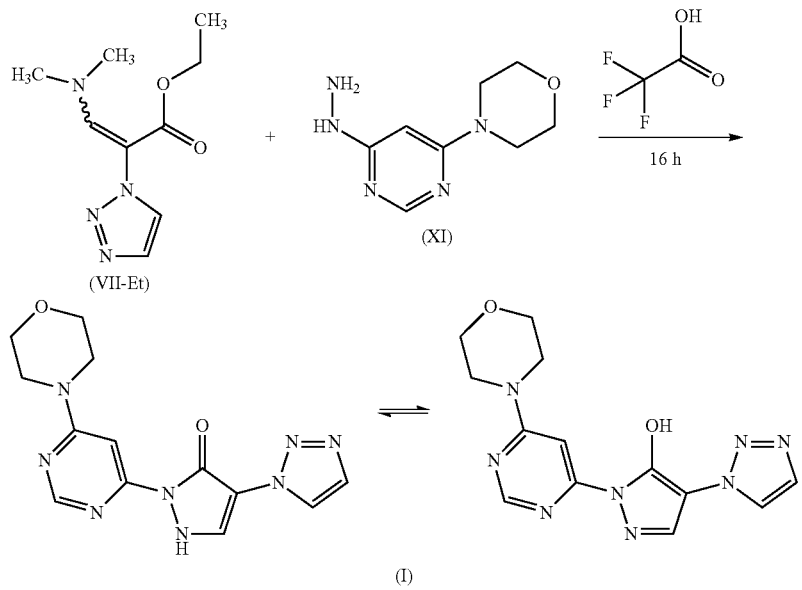

A synthesis of the compound of the formula (II) has hitherto not been described. Since the compound of the formula (II) is the sodium salt of the compound of the formula (I), it should be possible to prepare the compound of the formula (II) by reaction of the compound of the formula (I) with a basic sodium salt, for example sodium hydroxide:

Scheme 5

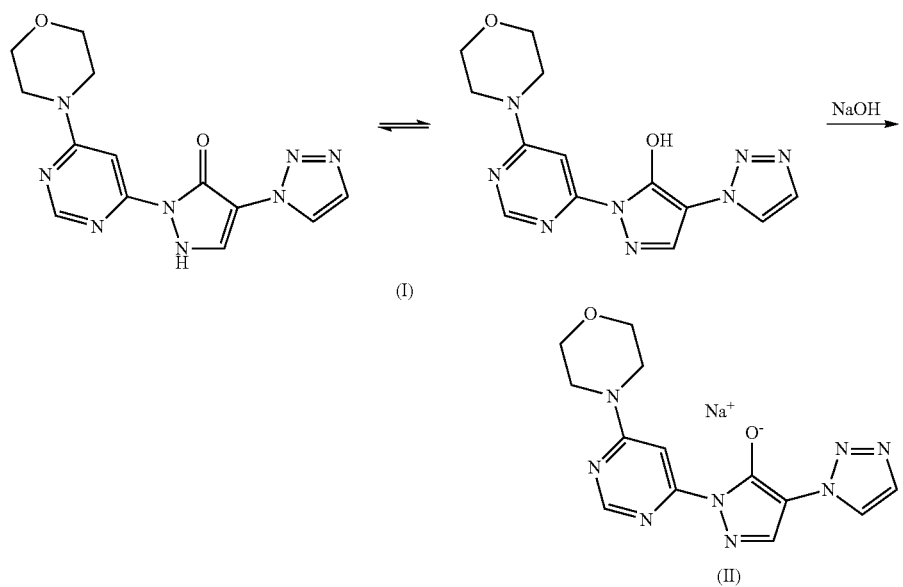

This leads to the object of the present invention, viz. to provide a process for preparing the compound of the formula (I) and the compound of the formula (II), which is, in particular, suitable for the production of relatively large amounts of product in good yield and with high purity.

Step a)

It has now surprisingly been found that the alkylation of 1,2,3-triazole (III) with an alkyl bromoacetate (IV-R-Br; R=methyl (Me), ethyl (Et)) using ethyldiisopropylamine as base leads to selectivities of ≥6:1 in favour of the desired alkyl 1H-1,2,3-triazol-1-ylacetate (V-R; R=methyl (Me), ethyl (Et)) based on the alkyl 2H-1,2,3-triazol-2-ylacetate (VI-R; R=methyl (Me), ethyl (Et)), without large excesses of the alkylating agent being necessary or low reaction conversions being achieved. This degree of selectivity is significantly higher than the values described hitherto for alkylations of 1,2,3-triazole (III). In particular, the greater selectivity of the alkylation also makes a higher total yield based on 1,2,3-triazole (III) possible in the preparation of the compound of the formula (I) or the compound of the formula (II). The reaction is generally carried out in inert solvents.

Scheme 6

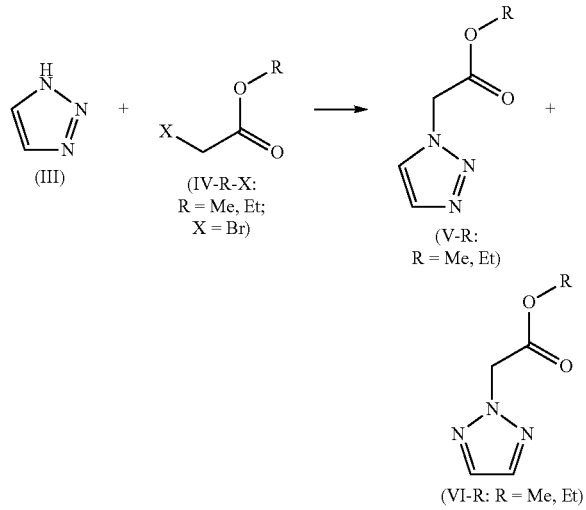

The reaction is preferably carried out using methyl bromoacetate (IV-Me-Br) or ethyl bromoacetate (IV-Et-Br), very particularly preferably using methyl bromoacetate (IV-Me-Br). The reaction is preferably carried out in an alkyl acetate of a short-chain alcohol (C-1 to C-4) as solvent, very particularly preferably in ethyl acetate as solvent. Particular preference is given to using from 0.9 to 1.8 molar equivalents, very particularly preferably from 1.1 to 1.3 molar equivalents, of the alkyl bromoacetate (IV-R-Br) based on 1,2,3-triazole (III). The reaction is preferably carried out at from 20 to 80° C., particularly preferably from 30 to 50° C., very particularly preferably from 35 to 45° C. Particular preference is given to using from 1.2 to 3 molar equivalents, very particularly preferably from 1.8 to 2.2 molar equivalents, of ethyldiisopropylamine. The alkyl bromoacetate (IV-R-Br) is preferably introduced over a period of from 0.5 to 16 hours to a stirred mixture of 1,2,3-triazole (III) and ethyldiisopropylamine in a solvent; this introduction is very particularly preferably carried out at a temperature of from 30 to 40° C. After introduction of the alkyl bromoacetate (IV-R-Br), the reaction mixture is preferably stirred further at from 30 to 50° C. for from 2 to 24 hours; the reaction mixture is very particularly preferably stirred further at from 35 to 45° C. for from 4 to 10 hours.

In a variant of the process, preference is given to using from 0.05 to 0.5 molar equivalent or very particularly preferably from 0.1 to 0.3 molar equivalent of ethyldiisopropylamine in the presence of from 1.0 to 2.0 molar equivalents of sodium hydrogencarbonate as base.

The salts formed in the reaction can be removed from the products by filtration or dissolution in water. Preference is given to separating off the salts by filtration of the reaction mixture via a suitable filter apparatus. This filtration is particularly preferably carried out at a temperature of from −5 to 25° C.

The solution of the product mixture obtained in this way can be concentrated by distillation and, for example, purified by crystallization. As an alternative and preferably, the solution of the product mixture of the compounds of the formulae (V-R) and (VI-R) is used without further purification in the reaction to form the compound of the formula (VII-R). Part of the solvent is very particularly preferably removed by distillation before the conversion into the compound of the formula (VII-R).

Furthermore, it has been found that in the alkylation of 1,2,3-triazole (III) with alkyl bromoacetate (IV-R-Br; R=methyl (Me), ethyl (Et)), high selectivities of ≥6:1 are achieved even when using from 1.5 to 3 equivalents of sodium hydrogencarbonate in acetonitrile. The reaction is preferably carried out in the temperature range from 30 to 90° C., particularly preferably in the temperature range from 50 to 70° C., and for a reaction time of from 16 to 48 h, particularly preferably a reaction time of from 20 to 30 hours.

It has surprisingly been found that the compounds of the formulae (VII-Me) and (VII-Et) can be obtained in relatively large amounts and high product quality in a simple process by reacting a solution of the crude products from the preparation of the compounds of the formulae (V-Me) and (VI-Me) or compounds of the formulae (V-Et) and (VI-Et), which are present in a ratio of at least 6:1 to one another, with dimethylformamide dimethyl acetal (XIX-Me) or dimethylformamide diethyl acetal (XIX-Et) in a first inert solvent at elevated temperature. The respective product from the compound of the formula (VII-Me) or the compound of the formula (VII-Et) is subsequently crystallized by cooling the solution or by distilling off the solvent and adding a second solvent. Before the crystallization, a third solvent is optionally added, the solution is filtered and the solvent is distilled off.

Scheme 7

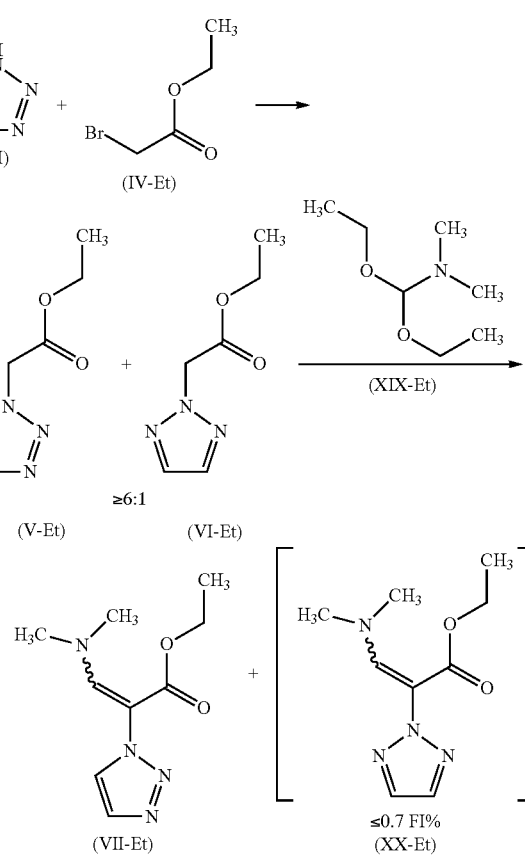

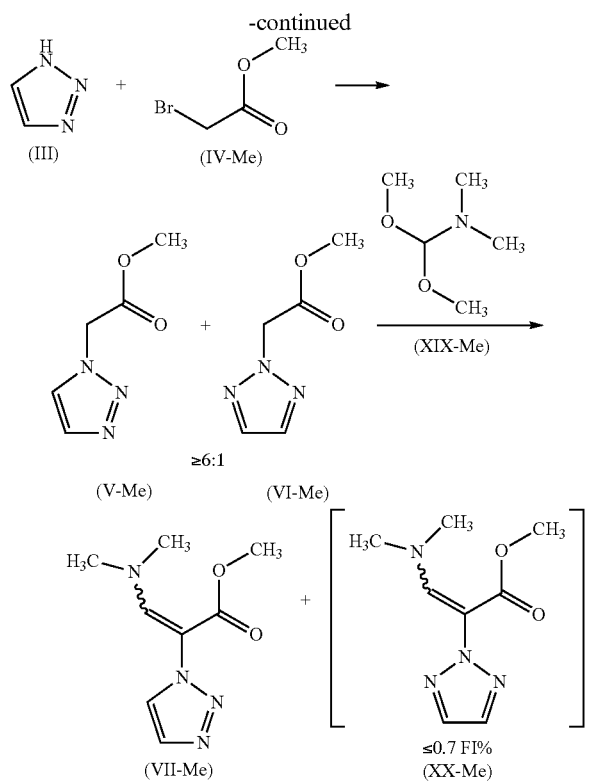

The reaction is preferably carried out using a solution of the crude products from the preparation of the compounds of the formulae (V-Me) and (VI-Me) which are present in a ratio of at least 6:1 to one another with dimethylformamide dimethyl acetal (XIX-Me).

The reaction is preferably carried out in a first inert solvent. The reaction is particularly preferably carried out in an alkyl acetate or alkyl alcohol, in which alkyl it is methyl, ethyl, 1-propyl, 1-butyl, 2-propyl, 2-butyl. As an alternative, dimethylformamide dimethyl acetal (XIX-Me) or dimethylformamide diethyl acetal (XIX-Et) can serve as solvent and reactant.

Based on the amount of 1,2,3-triazole (III) used in the respective alkylation, from 0.9 to 4.0 molar equivalents of dimethylformamide dimethyl acetal (XIX-Me) or dimethylformamide diethyl acetal (XIX-Et) are used. Preference is given to using from 1.1 to 3.0 molar equivalents, very particularly preferably from 1.2 to 2.0 molar equivalents, of dimethylformamide dimethyl acetal (XIX-Me) or dimethylformamide diethyl acetal (XIX-Et).

The reaction is carried out in the temperature range from 60 to 120° C. It is preferably carried out at from 70 to 90° C. The reaction mixture is preferably stirred for from 0.5 to 8 hours at the reaction temperature. The reaction mixture is particularly preferably stirred for from 1 to 6 hours at from 70 to 90° C. The reaction mixture is very particularly preferably stirred for from 2 to 4 hours at from 75 to 90° C.

The low boilers formed in the reaction are preferably distilled off.

After the reaction, a third solvent such as acetone, ethyl acetate or tetrahydrofuran is preferably added to the reaction mixture and the solution is filtered in order to remove solid impurities formed in the reaction. The filtration is particularly preferably carried out at a temperature of from 50 to 80° C.

The compounds of the formulae (VII-Me) and (VII-Et) are preferably crystallized from the previously filtered reaction mixture by cooling the solution to a temperature of from −5 to 25° C. and the crystals are isolated by subsequent filtration. Crystallization is preferably carried out from a second solvent such as isopropanol, ethyl acetate, acetone or methyl tert-butyl ether or a suitable mixture of these solvents. Crystallization is particularly preferably carried out from isopropanol. If the crystallization is carried out in a solvent other than that used in the reaction, the change of solvent is preferably carried out by distillation.

The quality of the compounds prepared in this way is sufficiently high for them to be able to be used without chromatographic purification processes in the preparation of the compound of the formula (I) or of the compound of the formula (II). In particular, the quality is characterized by a low content of the isomeric impurities of the compound of the formula (XX-Me) or of the compound of the formula (XX-Et). The achievement of a very low content of the respective isomeric impurities of the compound of the formula (XX-Me) or of the compound of the formula (XX-Et) by means of a simple process without multiple purification steps is an essential prerequisite for the compound of the formula (I) or of the compound of the formula (II) to be able to reliably attain the quality required of a pharmaceutical active compound even in the production of relatively large amounts without technically complicated purification operations being necessary.

Step b)

In addition, it has surprisingly been found that relatively large amounts of the compound of the formula (XI) can be prepared in a simple process, with good quality and without additional purification steps, e.g. chromatography, from 4,6-dichloropyrimidine (VIII), morpholine (IX) and only ≤2 molar equivalents of hydrazine hydrate (XII hydrate) (based on 4,6-dichloropyrimidine (VIII)) when, in the first stage, 4,6-dichloropyrimidine (VIII) is firstly reacted with hydrazine hydrate (XII hydrate) in a solvent, optionally in the presence of an auxiliary base, and the reaction mixture obtained is, without isolation of the compound of the formula (XV) formed, heated in a second stage after addition of morpholine (IX) and a further auxiliary base, and the compound of the formula (XI) is subsequently isolated by crystallization. Handling of the compound of the formula (XV) in a dry form capable of deflagration and large excesses of hydrazine hydrate (XII hydrate), which is toxic and has been found to cause cancer in test animals, can be avoided in this way.

Scheme 8

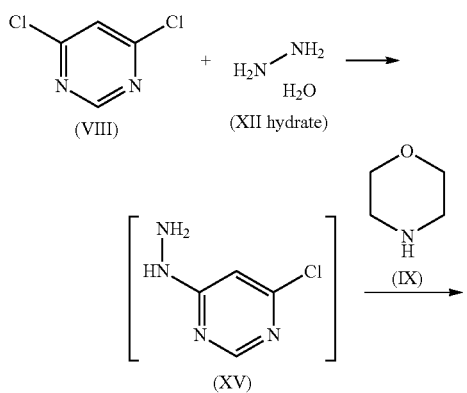

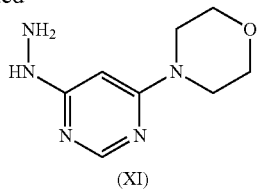

(XI)

The reaction is preferably carried out in water or an alkyl alcohol, in which alkyl is methyl, ethyl, 1-propyl, 1-butyl, 2-propyl, 2-butyl, or a mixture of these solvents. The reaction is particularly preferably carried out in water. Very particular preference is given to using from 2.4 to 3.8 kg of water per 1 kg of 4,6-dichloropyrimidine (VIII).

Based on 1 equivalent of 4,6-dichloropyrimidine (VIII), preference is given to using from 0.9 to 2.0 molar equivalents of hydrazine hydrate (XII hydrate) in the first stage of this process. Particular preference is given to using from 1.0 to 1.5 molar equivalents of hydrazine hydrate (XII hydrate) and from 1.0 to 1.5 molar equivalents of triethylamine or ethyldiisopropylamine as auxiliary base; very particular preference is given to using from 1.1 to 1.3 molar equivalents of hydrazine hydrate (XII hydrate) and from 1.1 to 1.3 molar equivalents of triethylamine as auxiliary base, based on 1 equivalent of 4,6-dichloropyrimidine (VIII).

The introduction of hydrazine hydrate (XII hydrate) to the 4,6-dichloropyrimidine (VIII) placed in the solvent and any auxiliary base used is preferably carried out at from 0 to 25° C., particularly preferably at from 10 to 20° C. In a variant of the process, the introduction of triethylamine or ethyldiisopropylamine to the 4,6-dichloropyrimidine (VIII) placed in the solvent and hydrazine hydrate (XII hydrate) is carried out at from 0 to 25° C., and the introduction of triethylamine is particularly preferably carried out at from 10 to 20° C.

The reaction mixture produced in this way in the first stage is preferably stirred at a temperature of from 10 to 30° C., particularly preferably from 20 to 25° C. The reaction time in the first stage is preferably from 2 to 24 hours, with the reaction mixture particularly preferably being stirred at from 20 to 25° C. for from 8 to 16 hours.

The 4-chloro-6-hydrazinopyrimidine (XV) produced in this way is preferably not isolated. The solution or suspension of 4-chloro-6-hydrazinopyrimidine (XV) obtained in this way is preferably converted directly to 4-(6-hydrazinopyrimidin-4-yl)morpholine (XI) by addition of morpholine (IX).

In the second stage, preference is given to adding from 0.9 to 1.5 molar equivalents of morpholine (IX), based on 4,6-dichloropyrimidine (VIII) used, are preferably added to the reaction mixture from the first stage. Particular preference is given to adding from 1.0 to 1.3 molar equivalents of morpholine (IX), based on 4,6-dichloropyrimidine (VIII), to the reaction mixture.

An additional inorganic auxiliary base, e.g. sodium hydrogencarbonate, potassium hydrogencarbonate, sodium hydroxide or potassium hydroxide, is preferably used in the reaction with morpholine (IX) in the second stage. Particular preference is given to using from 1.0 to 2.0 molar equivalents of sodium hydrogencarbonate, very particularly preferably from 1.1 to 1.3 molar equivalents of sodium hydrogencarbonate.

To form 4-(6-hydrazinopyrimidin-4-yl)morpholine (XI), the morpholine (IX) containing reaction mixture of the second stage is preferably stirred at a temperature of from 70 to 110° C. and particularly preferably at from 75 to 95° C. The reaction time is preferably from 4 to 24 hours. The reaction mixture is particularly preferably stirred at from 75 to 95° C. for from 6 to 10 hours.

4-(6-Hydrazinopyrimidin-4-yl)morpholine (XI) is preferably isolated after the reaction by crystallization and filtration. The filtration is particularly preferably carried out at a temperature of from 5 to 25° C. The compound of the formula (XI) obtained is preferably washed with water.

Step c)

In addition, it has surprisingly been found that the compound of the formula (I) can be prepared in relatively large amounts with good yield and very good quality by a simple process which can be carried out industrially.

Scheme 9

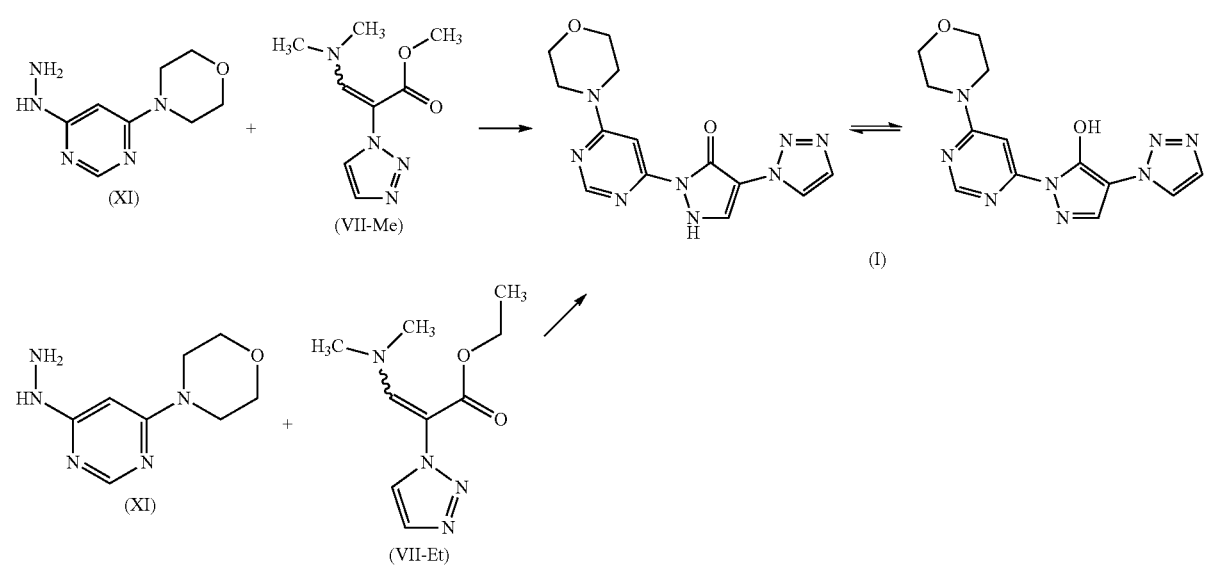

For this purpose, 4-(6-hydrazinopyrimidin-4-yl)morpholine (XI) and one of the compounds of the formulae (VII-Me) and (VII-Et) are preferably reacted in the presence of an acid and in an inert solvent. Particular preference is given to reacting 4-(6-hydrazinopyrimidin-4-yl)morpholine (XI) and methyl (2E/Z)-3-(dimethylamino)-2-(1H-1,2,3-triazol-1-yl)acrylate (VII-Me) in the presence of an acid and in an inert solvent.

As solvent, preference is given to using an alkyl ester of formic acid, acetic acid or propionic acid, an alkyl alcohol or an alkyl cyanide, where alkyl is methyl, ethyl, 1-propyl, 1-butyl, 2-propyl, 2-butyl, or a suitable mixture of these solvents. Particular preference is given to using ethyl acetate, n-butyl acetate or n-butyronitrile as solvent.

Trifluoroacetic acid is preferably used as acid. Particular preference is given to using from 0.2 to 1.0 molar equivalent of trifluoroacetic acid, based on 4-(6-hydrazinopyrimidin-4-yl)morpholine (XI). Very particular preference is given to using from 0.4 to 0.6 molar equivalent of trifluoroacetic acid, based on 4-(6-hydrazinopyrimidin-4-yl)morpholine (XI).

The compounds of the formulae (VII-Me) and (VII-Et) are preferably used in an amount of from 0.9 to 1.5 molar equivalents based on 4-(6-hydrazinopyrimidin-4-yl)morpholine (XI). The compounds of the formulae (VII-Me) and (VII-Et) are particularly preferably used in an amount of from 1.0 to 1.2 molar equivalents based on 4-(6-hydrazinopyrimidin-4-yl)morpholine (XI).

The reaction is preferably carried out in the temperature range from 70 to 140° C. The reaction is particularly preferably carried out in the temperature range from 75 to 120° C.

The reaction time in ethyl acetate is preferably from 20 to 30 hours at from 75 to 90° C. and the reaction time in n-butyl acetate or n-butyronitrile is preferably from 5 to 10 hours at from 110 to 120° C.

To isolate a crude product of the formula (I), the reaction mixture is preferably cooled to from 0 to 25° C. and filtered. This filtration is particularly preferably carried out at from 0 to 10° C.

The crude product of the formula (I) obtained is preferably mixed with water and an acid to effect purification and the mixture obtained is filtered again. The purification using water and an acid is particularly preferably carried out at a pH of from 4 to 5.5. The purification using water and acetic acid is very particularly preferably carried out at a pH of from 4 to 5.5.

The product of the formula (I) isolated by filtration is preferably dried under reduced pressure.

In a variant of the process for preparing the compound of the formula (I), the reaction mixture consisting of the compounds of the formulae (VII-Me) or (VII-Et) and 4-(6-hydrazinopyrimidin-4-yl)morpholine (XI) and also trifluoroacetic acid in a solvent is, after a first reaction time in the temperature range from 60 to 120° C., preferably from 70 to 90° C., admixed with a base. In this variant of the process, preference is given to using from 1.0 to 1.5 molar equivalents of trifluoroacetic acid based on 4-(6-hydrazinopyrimidin-4-yl)morpholine (XI). The first reaction time before addition of the base is preferably from 2 to 5 hours. Preference is given to using ethyl acetate as solvent.

In this variant of the process, a tertiary amine is preferably used as base. Very particular preference is given to using triethylamine as base.

In this variant of the process, preference is given to using from 1.5 to 3 molar equivalents of the base based on 4-(6-hydrazinopyrimidin-4-yl)morpholine (XI) used. Particular preference is given to using from 1.8 to 2.7 molar equivalents of the base based on 4-(6-hydrazinopyrimidin-4-yl)morpholine (XI) used.

In this variant of the process, the reaction mixture after addition of the base is preferably maintained at a temperature of from 20 to 90° C., particularly preferably at a temperature of from 50 to 80° C.

In this variant of the process, the reaction time after addition of the base is preferably from 1 to 12 hours, very particularly preferably from 2 to 5 hours.

In this variant of the process, the reaction mixture is preferably cooled to from −10 to 25° C. and filtered in order to isolate a crude product of the formula (I). This filtration is particularly preferably carried out at from 0 to 10° C.

The resulting crude product of the compound of the formula (I) is preferably mixed with water and an acid to effect purification and the mixture obtained is filtered again. The purification using water and an acid is particularly preferably carried out at a pH of from 4 to 5.5. The purification using water and acetic acid is very particularly preferably carried out at a pH of from 4 to 5.5.

The product of the formula (I) isolated by filtration is preferably dried under reduced pressure.

It has surprisingly been found that the compound of the formula (II) can be prepared in relatively large amounts with very good yields and very good quality from the compound of the formula (I) in a simple process by reaction with sodium hydroxide or aqueous sodium hydroxide solution or sodium methoxide or sodium ethoxide or a sodium salt.

Scheme 10

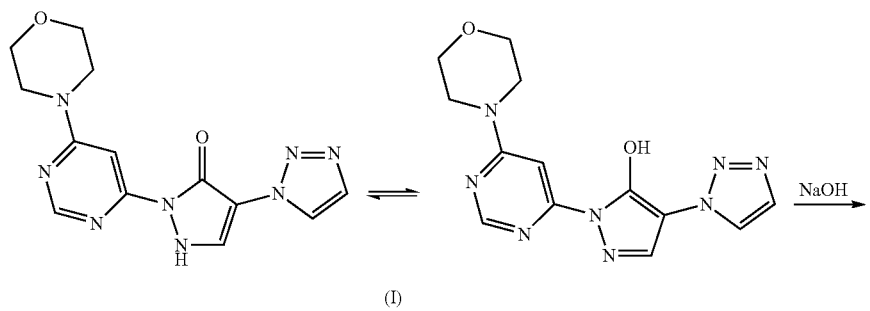

(I)

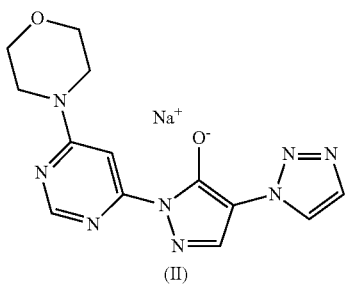

(II)

The compound of the formula (I) is preferably firstly dissolved in a suitable solvent in the first stage by addition of an organic base and filtered to separate off any insoluble constituents present. The optionally filtered solution of the compound of the formula (I) is, in a second stage, reacted with sodium hydroxide or aqueous sodium hydroxide solution or sodium methoxide or sodium ethoxide or a sodium salt.

Suitable solvents are lower alcohols such as methanol, ethanol, n-propanol, isopropanol, n-butanol, sec-butanol, isobutanol, 1-pentanol, or tetrahydrofuran, or acetonitrile, or acetone, or toluene, or 1,4-dioxane or mixtures of the solvents mentioned, or mixtures of the solvents mentioned with water. Preference is given to methanol, ethanol, 2-propanol, tetrahydrofuran or mixtures of the solvents mentioned with water. Particular preference is given to mixtures of methanol or ethanol with water in a ratio in the range from 1:1 to 50:1 (v/v), with very particular preference being given to mixtures of methanol with water in a ratio in the range from 7:3 to 30:1 (v/v).

Suitable organic bases in the first stage are tertiary amines such as triethylamine or diisopropylethylamine. Preference is given to triethylamine. The organic base is used in a ratio of from 0.9 to 4 molar equivalents based on the compound of the formula (I). The organic base is preferably used in a ratio of from 0.7 to 1.5 molar equivalents based on the compound of the formula (I). The organic base is very particularly preferably used in a ratio of from 0.9 to 1.2 molar equivalents based on the compound of the formula (I).

The dissolution of the compound of the formula (I) and the filtration are particularly preferably carried out at a temperature of from 40 to 120° C., the dissolution of the compound of the formula (I) and the filtration are very particularly preferably carried out at a temperature of from 40 to 80° C.

The reaction with sodium hydroxide or aqueous sodium hydroxide solution or sodium methoxide or sodium ethoxide or a sodium salt in the second stage is preferably carried out in the temperature range from 20 to 120° C., particularly preferably in the temperature range from 40 to 70° C., at atmospheric pressure. The compound the formula (II) is isolated from the resulting suspension by filtration at a temperature in the range from −20 to 80° C., preferably at a temperature of from 0 to 20° C., at atmospheric pressure and subsequently dried.

Sodium hydroxide and aqueous sodium hydroxide solution and sodium methoxide and sodium ethoxide and the sodium salt are used in a molar ratio of from 0.8 to 2 molar equivalents based on the compound of the formula (I). Sodium hydroxide and aqueous sodium hydroxide solution and the sodium salt are preferably used in a molar ratio of from 1.0 to 1.4 molar equivalents based on the compound of the formula (I).

Suitable sodium salts are, for example, salts of organic acids, e.g. sodium carboxylates such as sodium acetate or sodium citrate, or salts of inorganic acids, for example sodium carbonate, sodium hydrogencarbonate, sodium phosphate, sodium hydrogenphosphate or sodium chloride. Particular preference is given to using aqueous sodium hydroxide solution or sodium methoxide or sodium ethoxide. Very particular preference is given to using aqueous sodium hydroxide solution.

The invention further provides a process for preparing 1-[6-(morpholin-4-yl)pyrimidin-4-yl]-4-(1H-1,2,3-triazol-1-yl)-1H-pyrazol-5-ol (I—enol form) or 2-[6-(morpholin-4-yl)pyrimidin-4-yl]-4-(1H-1,2,3-triazol-1-yl)-1,2-dihydro-3H-pyrazol-3-one (I—keto form), characterized in that a) in the first step, 1,2,3-triazole (III) is reacted with methyl bromoacetate (IV-Me-Br) or ethyl bromoacetate (IV-Et-Br) in the presence of ethyldiisopropylamine as base in a solvent in the temperature range from 20 to 80° C. to form compounds of the formulae (V-Me) and (VI-Me) or compounds of the formulae (V-Et) and (VI-Et), b) in the second step, compounds of the formulae (V-Me) and (VI-Me) or compounds of the formulae (V-Et) and (VI-Et), which are present in a ratio of at least 6:1 to one another, are reacted with dimethylformamide dimethyl acetal (XIX-Me) or dimethylformamide diethyl acetal (XIX-Et) in an inert solvent and are subsequently crystallized by cooling the solution or by distilling off the solvent and adding a second solvent to form methyl (2E/Z)-3-(dimethylamino)-2-(1H-1,2,3-triazol-1-yl)acrylate (VII-Me) or ethyl (2E/Z)-3-(dimethylamino)-2-(1H-1,2,3-triazol-1-yl)acrylate (VII-Et), and c) in the third step, methyl (2E/Z)-3-(dimethylamino)-2-(1H-1,2,3-triazol-1-yl)acrylate (VII-Me) or ethyl (2E/Z)-3-(dimethylamino)-2-(1H-1,2,3-triazol-1-yl)acrylate (VII-Et) is reacted with 4-(6-hydrazinopyrimidin-4-yl)morpholine (XI) in the presence of trifluoroacetic acid in an inert solvent and the compound of the formula (I) is subsequently isolated.

The invention further provides a process for preparing methyl (2E/Z)-3-(dimethylamino)-2-(1H-1,2,3-triazol-1-yl)acrylate (VII-Me) or ethyl (2E/Z)-3-(dimethylamino)-2-(1H-1,2,3-triazol-1-yl)acrylate (VII-Et), characterized in that compounds of the formulae (V-Me) and (VI-Me) or compounds of the formulae (V-Et) and (VI-Et), which are present in a ratio of at least 6:1 to one another, are reacted with dimethylformamide dimethyl acetal (XIX-Me) or dimethylformamide diethyl acetal (XIX-Et) in an inert solvent and are subsequently crystallized by cooling the solution or by distilling off the solvent and adding a second solvent, where compounds of the formulae (V-Me) and (VI-Me) or compounds of the formulae (V-Et) and (VI-Et) are prepared by reacting 1,2,3-triazole (III) with methyl bromoacetate (IV-Me-Br) or ethyl bromoacetate (IV-Et-Br) in the presence of ethyldiisopropylamine as base in a solvent in the temperature range from 20 to 80° C.

The invention further provides methyl (2E/Z)-3-(dimethylamino)-2-(1H-1,2,3-triazol-1-yl)acrylate having the formula

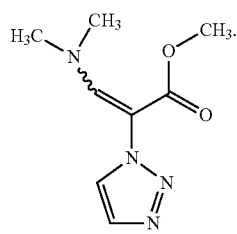

(VII-Me)

The individual steps of the process of the invention can be carried out at atmospheric, superatmospheric or reduced pressure (e.g. from 0.5 to 5 bar). Unless indicated otherwise, the operations are generally carried out at atmospheric pressure.

The invention is illustrated below by a preferred illustrative example, but is not restricted thereto. Unless indicated otherwise, all amounts are percentages by weight.

EXAMPLES

Abbreviations and Acronyms wt % percent by weight
area % percent by area
% o. th. percent of theory
corr. corrected
uncorr. uncorrected
min minutes
h hours
mg milligramme
g gramme
kg kilogramme
l liter
ml milliliter
GC gas chromatography
HPLC high pressure (performance) liquid chromatography
s singlet
d doublet
m multiplet
Hz hertz
HPLC Method for the Compounds of the Formulae (I) and (II)
Reversed-phase method; detection: UV range
Equipment: High-performance liquid chromatograph with thermostatted column oven, UV detector and data evaluation system;
Metal column made of stainless steel: length: 15 cm; internal diameter: 3.0 mm; packing: e.g. Poroshell 120 EC-C18, 2.7 µm, or comparable;
Reagents: trifluoroacetic acid, for HPLC; acetonitrile, for HPLC; ethyl 4-hydroxybenzoate, 99%;
Test solution: about 25 mg of sample, weighed accurately, dissolved in water/acetonitrile (1:1 v/v) to 100.0 ml.
Calibration solution: about 25 mg of reference standard, weighed accurately, dissolved in water/acetonitrile (1:1 v/v) to 100.0 ml.

Comparison solution: A comparison solution analogous to the calibration solution but additionally containing the organic impurities in a small amount corresponding to the specification limit is prepared.

HPLC conditions: The conditions indicated are guidelines and may have to be adapted to the technical possibilities of the chromatograph and the properties of the respective column in order to achieve optimal separations.

Eluent: A. 0.2% strength trifluoroacetic acid (2.0 ml of trifluoroacetic acid dissolved in water to 1000 ml); B. 0.2% strength trifluoroacetic acid in acetonitrile (2.0 ml of trifluoroacetic acid dissolved in acetonitrile to 1000 ml); flow rate: 0.5 ml/min;

Temperature of the column oven: 35° C.; detection: measurement wavelength 280 nm, band width: 6 nm; injection volume: 3.0 µl; equilibration time: 10 min (under start conditions); running time of the chromatogram: 30 min.

| Gradient | | |
|---|---|---|
| Time [min] | % A | % B |
| 0 | 95 | 5 |
| 20 | 60 | 40 |
| 25 | 20 | 80 |
| 30 | 20 | 80 |

GC Method for the Compounds of the Formulae (V), (VI), (VII) and (XX)

Equipment/detector: Gas chromatograph with electronic pressure control, autosampler, FID and data evaluation system
Injector temperature: 250° C.
Liner: Focus liner, 4 mm ID, 78.5×6.3 mm OD, from SGE, part No.: 092219
Column flow: 2 ml/min (constant flow mode)
Split ratio/split flow: 20/40 ml/min
Column: HP5 MS UI (fused silica, 5% phenylmethylsiloxane); length: 30 m, internal diameter: 0.32 mm, film thickness: 1.0 µm
Carrier gas: Helium
Temperature programme: Initial temperature: 40° C.; initial time: 0 min; rate 10° C./min, final 100° C., hold time 5 min; rate 10° C./min, final 300° C., hold time 4 min;
Total (total running time): 35 min
Detector temperature: 310° C.
Combustion gases: Oxidizer flow (synthetic air): 450 ml/min; fuel flow (hydrogen): 40 ml/min; make-up (nitrogen): 30 ml/min
Data rate: 10 Hz
Sample solvent: water+acetonitrile (2+8 V/V)
Test solution/calibration solution: dissolved about 5 mg/ml of the substance with solvent in an ultrasonic bath and make up to the mark.
Comparison solution: Comparison solutions analogous to the calibration solution but additionally containing the organic impurities in a small amount are prepared.
Injection volume: 1.0 µl
GC Method for the Compounds of the Formulae (XI) and (XV)
Equipment/detector: Gas chromatograph with electronic pressure control, autosampler, FID and data evaluation system
Injector temperature: 250° C.
Liner: Focus liner, 4 mm ID, 78.5×6.3 mm OD, from SGE, part No.: 092219
Column flow: 2 ml/min (constant flow mode)

Split ratio/split flow: 20/40 ml/min
Column: HP5 MS UI (fused silica, 5% phenylmethylsiloxane); length: 30 m, internal diameter: 0.32 mm, film thickness: 1.0 μm
Carrier gas: Helium
Temperature programme: Initial temperature: 40° C.; initial time: 0 min; rate 10° C./min, final 100° C., hold time 5 min; rate 10° C./min, final 300° C., hold time 4 min;
Total (total running time): 35 min
Detector temperature: 310° C.
Combustion gases: Oxidizer flow (synthetic air): 450 ml/min; fuel flow (hydrogen): 40 ml/min; make-up (nitrogen): 30 ml/min
Data rate: 10 Hz
Sample solvent: water+acetonitrile (1+1 V/V)
Test solution/calibration solution: dissolve about 5 mg/ml of the substance with solvent in an ultrasonic bath and make up to the mark.
Comparison solution: The comparison solutions are prepared individually and injected individually.
Injection volume: 1.0 μl
Ion Chromatography for Determining Anionic Impurities
Equipment: Sympatec Helos; Dispersion medium: dry; pressure: 58 psi (4 bar)
Acetate, bromide, trifluoroacetate; ion chromatography in accordance with AM-AAL 61
Equipment: Ion chromatograph with suppressor system, conductivity detector and chromatography data system;
Precolumn: A SUPP 4/5 Guard;
Column: Separation phase: A SUPP 5; length: about 250 mm; internal diameter: about 4.0 mm;
Reagents: Methanol, for HPLC; sodium carbonate, AR, sodium hydrogencarbonate, AR, Milli-Q water, sulphuric acid, Suprapur;
Test solution: Concentration: 0.1%; (e.g. 50 mg/50 ml standard flask); the sample is dissolved in 20% of the total volume of methanol, treated for three minutes in an ultrasonic bath and made up to the mark with water. The solution is subsequently filtered through an ion-free cellulose acetate filter (0.45 μm pore size).
Calibration solutions: Absolute concentration: from 0.5 mg/l to 10 mg/l;
IC conditions: The conditions indicated are guidelines and may have to be adapted to the technical possibilities of the chromatograph and the properties of the respective column in order to achieve optimal separations.
Eluent: 3.2 mmol of sodium carbonate, 2.4 mmol of sodium hydrogencarbonate/liter of water;
Flow rate: 0.7 ml/min;
Detector: Conductivity detector;
Range: 10 mS/cm;
Full scale: 50 μS/cm;
Suppressor: Water/50 mmol of sulphuric acid;
Injection volume: 20 μl (fixed loop)
Running time of the chromatogram: 30 min
Procedure: Chromatograph test solution and calibration solutions under the conditions indicated. The peaks to be determined and detected in the chromatogram of the test solution have to agree in terms of the retention times with the peaks in the chromatogram of the calibration solutions.

| Anion | RT [min] |
|---|---|
| Acetate | about 6 |
| Trifluoroacetate | about 13 |
| Bromide | about 14 |

Evaluation: Electronic integration of the peak areas.
Calculation: External standard method (ESTD) with quadratic regression.

Working Examples

Synthesis of 4-(6-hydrazinopyrimidin-4-yl)morpholine (XI)

Example 1

35.0 kg (234.9 mol) of 4,6-dichloropyrimidine were suspended in 82 kg of water at 20° C. in a stirred vessel, admixed with 28.5 kg (281.6 mol) of triethylamine and a further 5 kg of water, then cooled to 12° C. 14.0 g (279.4 mol) of hydrazine hydrate were subsequently introduced at from 12 to 14° C. over a period of about 1 hour. A further 5 kg of water were added, the mixture was stirred for another 3 hours at 12° C. and was then warmed to 20° C. After 16 hours at 20° C., 23.8 kg (283.3 mol) of sodium hydrogencarbonate, then 23.6 kg (270.9 mol) of morpholine and 5 kg of water were added. The mixture was heated at a jacket temperature of 90° C. and stirred for 9 hours. The solution obtained was cooled to 70° C. and inoculated with 0.14 kg of 4-(6-hydrazinopyrimidin-4-yl)morpholine, then cooled to 3° C. over a period of 5 hours. The suspension obtained was stirred at 3° C. for 3 hours, cooled to 5° C. and filtered in a number of portions in a peeler centrifuge. The product cake was in each case washed with cold water and dried at 40° C. for about 8 hours under reduced pressure in a mixer-dryer. Yield: 32.9 kg (71.7% of theory) of the compound of the formula (XI), 98.5% by weight, 0.5 area % total impurities, 26 ppm of hydrazine MS (ESIpos): m/e=196.0 [M+H]$^+$;
$^1$H NMR (500, 13 MHz, d$_6$-DMSO): 7.95 ppm (bs, 1H), 7.68 (bs, 1H), 5.92 (bs, 1H), 4.14 (bs, 2H), 3.64 (t, 4H), 3.43 (t, 4H).

Example 2

50.65 g (0.34 mol) of 4,6-dichloropyrimidine were suspended in 140 ml of water and cooled to 12° C. 20.4 g (0.41 mol) of hydrazine hydrate and subsequently 41.3 g (0.41 mol) of triethylamine were added at 12-15° C. The mixture was stirred at 12° C. for a further 2 hours and warmed to 20° C. over a period of 3 hours. After 16 hours at 20° C., 34.3 g (0.41 mol) of sodium hydrogencarbonate and then 34.1 g (0.39 mol) of morpholine were added. The mixture was heated to 80° C., stirred for 7 hours at 80° C. and 2 hours at 82° C., with low boilers being distilled off. The solution obtained was cooled to 20° C. over a period of 3 hours. The solution was inoculated with product crystals at an internal temperature of from about 70 to 76° C. The suspension obtained was stirred at 20° C. for about 12 hours and subsequently filtered. The product cake was washed twice with 25 ml each time of water and dried at 40° C. under reduced pressure for at least 16 hours. Yield: 43.5 g (65.5% of theory) of the compound of the formula (XI), 97.8% by weight.

Example 3

50.65 g (0.34 mol) of 4,6-dichloropyrimidine were suspended in 150 ml of water and cooled to 12° C. 41.3 g (0.41 mol) of triethylamine and subsequently 20.4 g (0.41 mol) of hydrazine hydrate were added at from 12 to 15° C. The mixture was stirred for another 2 hours at 12° C. and warmed to 20° C. over a period of 3 hours. After about 20 hours at 20° C., 34.3 g (0.41 mol) of sodium hydrogencarbonate and then 34.1 g (0.39 mol) of morpholine were added. The mixture was heated to about 78° C. and stirred at 78° C. for 9 hours. The solution obtained was cooled to 20° C. over a period of 5 hours. The suspension obtained was stirred at 20° C. for about 16 hours and subsequently filtered. The product cake was washed three times with 15 ml each time of water and dried at 40° C. under reduced pressure. Yield: 51.7 g (78% of theory) of the compound of the formula (XI), 97% by weight.

Example 4

50.65 g (0.34 mol) of 4,6-dichloropyrimidine were dissolved in 500 ml of methanol and cooled to 0° C. 41.3 g (0.41 mol) of triethylamine and subsequently 20.4 g (0.41 mol) of hydrazine hydrate were added at from 0 to 10° C. The mixture was stirred at 0° C. for another 2 hours and warmed to 20° C. After 1 hour at 20° C., 41.3 g (0.41 mol) of triethylamine and then 34.1 g (0.39 mol) of morpholine were added. The mixture was stirred under reflux for about 70 hours. The solution obtained was cooled to 20° C. The solution was inoculated with product crystals at an internal temperature of about 30° C. The suspension obtained was stirred at 20° C. for about 16 hours and subsequently filtered. The product cake was washed twice with 20 ml each time of methanol and dried at 40° C. under reduced pressure for at least 16 hours. Yield: 41 g (62% of theory without taking into account the content) of the compound of the formula (XI), about 80% by weight.

Example 5

50.65 g (0.34 mol) of 4,6-dichloropyrimidine were placed together with 340 ml of isopropanol and 160 ml of water in a reaction vessel. 41.3 g (0.41 mol) of triethylamine were added thereto and the mixture was cooled to 10° C. 20.4 g (0.41 mol) of hydrazine hydrate were subsequently added at from 10 to 15° C. The mixture was stirred at from 10 to 15° C. for a further 2 hours and then warmed to 20° C. After 3 hours at 20° C., 34.3 g (0.41 mol) of sodium hydrogencarbonate and then 41.5 g (0.48 mol) of morpholine were added. The mixture was heated to boiling and about 400 ml of solvent were distilled off. The mixture was subsequently stirred further at 84° C. for about 6 hours. The solution obtained was cooled to 20° C. The suspension obtained was stirred further at 20° C. and subsequently filtered. The product cake was washed three times with 10 ml each time of water and dried at 40° C. under reduced pressure. Yield: 40.5 g (61% of theory) of the compound of the formula (XI), 99% by weight.

Synthesis of methyl 1H-1,2,3-triazol-1-ylacetate (V-Me) and methyl 2H-1,2,3-triazol-1-ylacetate (VI-Me)

Example 6

1.34 kg (8.7 mol) of methyl bromoacetate were added dropwise to a solution of 1.87 kg (14.4 mol) of ethyldiisopropylamine and 500 g (7.2 mol) of 1,2,3-triazole in 5 l of ethyl acetate over a period of from 2.5 to 3 hours in such a way that the internal temperature was kept below 43° C. The reaction mixture was subsequently stirred for 2.5 hours at from 40 to 44° C., a further 16 hours at room temperature and then 15 minutes at 10° C. The suspension obtained was filtered, the filter cake was washed with 1.5 l of ethyl acetate and the combined filtrates were concentrated under reduced pressure (to 30 mbar) at 45° C. Yield: 1.24 kg of orange-red oil (125% of theory, uncorrected), isomer ratio 7.6:1 (compound of the formula (V-Me): compound of the formula (VI-Me); gas chromatography); complete conversion of 1,2,3-triazol, still contained ethyldiisopropylamine and ethyldiisopropylammonium hydrobromide.

MS (EI+): m/e=141.0 [M]+;
$^1$H NMR (500, 13 MHz, $d_6$-DMSO): 8.13 ppm (s, 1H, (V-Me)), 7.77 ppm (s, 1H, (V-Me)), 5.43 ppm (s, 2H, (V-Me)), 3.71 ppm (s, 3H, (V-Me)) and signals having a reduced area for (VI-Me) at 7.86 ppm (s, 2H, ((VI-Me)), 5.47 ppm (s, 2H, ((VI-Me)), 3.69 ppm (s, 3H, ((VI-Me)).

Example 7

130.2 g (0.84 mol) of methyl bromoacetate were added dropwise to a solution of 181.5 g (1.4 mol) of ethyldiisopropylamine and 50 g (0.7 mol) of 1,2,3-triazole in 500 ml of ethyl acetate at from 20 to 30° C. over a period of 30 minutes. The reaction mixture was subsequently stirred at 40° C. for 2 hours. Isomer ratio 8.9:1 (compound of the formula (V-Me): compound of the formula (VI-Me); gas chromatography); still contained about 2% of unreacted 1,2,3-triazol.

Example 8

8.5 g (101 mmol) of sodium hydrogencarbonate were suspended in 50 ml of acetone and admixed with 5 g (72 mmol) of 1,2,3-triazole. 9.7 ml (101 mmol) of methyl bromoacetate were slowly added at about 22° C. and the mixture was firstly stirred at about 22° C. for about 16 hours and subsequently at 40° C. for a further 3 days. The mixture was cooled to room temperature and filtered, the filter cake was washed with acetone. The combined filtrates were evaporated under reduced pressure to give a yellow oil. Yield: 15.1 g (148% of theory, uncorrected); isomer ratio 8.4:1 (compound of the formula (V-Me): compound of the formula (VI-Me); gas chromatography), contained about 8% of unreacted 1,2,3-triazole and also inorganic salts.

Example 9

121.6 g (1.45 mol) of sodium hydrogencarbonate were suspended in 500 ml of acetonitrile and admixed with 51.5 g (0.724 mol) of 1,2,3-triazole. 97.3 ml (1.01 mol) of methyl bromoacetate were added at about 60° C. over a period of 30 minutes and the mixture was firstly stirred at 60° C. for about 20 hours. The mixture was cooled to room temperatures and filtered, and the filter cake was washed with acetonitrile. The combined filtrates were evaporated under reduced pressure to give a yellow oil. Yield: 147.8 g (145% of theory, uncorrected); isomer ratio 7.5:1 (compound of the formula (V-Me): compound of the formula (VI-Me); gas chromatography), still contained about 4% of unreacted 1,2,3-triazole and also inorganic salts.

Synthesis of methyl (2E/Z)-3-(dimethylamino)-2-(1H-1,2,3-triazol-1-yl)acrylate (VII-Me)

Example 10

In a stirred vessel, 53.6 kg (4.3 mol) of methyl bromoacetate were added dropwise to a solution of 74.9 kg (579.5 mol) of ethyldiisopropylamine and 20 kg (289.6 mol) of 1,2,3-triazole in 184.3 kg of ethyl acetate at 35° C. over a period of about 2 hours in such a way that the internal temperature was kept at from 35 to 37° C. The reaction mixture was subsequently stirred at 40° C. for 8 hours. After cooling to 10° C., the suspension obtained was filtered, the filter cake was washed with 53.3 kg of ethyl acetate and the combined filtrates were concentrated at up to 60° C. under reduced pressure (255 kg of distillate). The evaporation residue (max. 289.6 mol) was admixed at 40° C. with 53.1 kg (445.6 mol) of N,N-dimethylformamide dimethyl acetal and stirred at from 80 to 86° C. for 2 hours. Low boilers formed were distilled off during this (16 kg of distillate). The mixture was subsequently cooled to 50° C., 122 kg of acetone were added, the mixture was maintained at 50° C. and undissolved constituents were filtered off hot. The filter cake was washed once with 19 kg of acetone (50° C.). The combined filtrates were concentrated by distillation (97 kg of distillate), admixed with 47 kg of isopropanol, once again concentrated by distillation at atmospheric pressure until a temperature of about 83° C. had been reached (60 kg of distillate), cooled to 70° C. and admixed with 16 kg of isopropanol. The mixture was inoculated with 0.15 kg of methyl (2E/Z)-3-(dimethylamino)-2-(1H-1,2,3-triazol-1-yl) acrylate and cooled to 0° C. over a period of 7 hours. After a further hour at 0° C., the mixture was filtered, the filter cake was washed twice with a mixture, which had been cooled to 0° C., of 16 kg of tert-butyl methyl ether and 16 kg of isopropanol and dried at 40° C. under reduced pressure. Yield: 43.0 kg (75.7% of theory, based on 1,2,3-triazole) of the compound of the formula (VII-Me), 98.2% by weight, 0.29 area % of isomer (GC), 0.2% by weight of bromide.

MS (ESIpos): m/e=197.0 [M+H]$^+$;

$^1$H NMR (500, 13 MHz, d$_6$-DMSO): 8.10 ppm (d, 1H), 7.78 (d, 1H), 7.67 (s, 1H), 3.55 (s, 3H), 3.4-2.4 (very broad s, 3H), 2.4-1.7 (very broad s, 3H)

Example 11

67.1 g (0.43 mol) of methyl bromoacetate were added dropwise to a solution of 95.5 g (0.72 mol) of ethyldiisopropylamine and 25 g (0.36 mol) of 1,2,3-triazole in 260 ml of ethyl acetate over a period of about 2 hours in such a way that the internal temperature was kept at 35° C. The reaction mixture was subsequently stirred for 6 hours at 40° C. and a further 16 hours at 0° C. The suspension obtained was filtered, the filter cake was washed with 60 ml of ethyl acetate and the combined filtrates were concentrated at 40° C. under reduced pressure (at 230 mbar). The evaporation residue (59.5 g; 117.1% of theory, uncorrected, max. 0.36 mol) was admixed at 35° C. with 66 g (1.08 mol) of N,N-dimethylformamide dimethyl acetal and stirred at from 83 to 90° C. for 2 hours. Low boilers formed were distilled off during this. The mixture was subsequently cooled to 50° C., 200 ml of acetone were added, undissolved constituents were filtered off hot and washed twice with 25 ml each time of acetone. The combined filtrates were concentrated by distillation, admixed with 75 ml of isopropanol, once again concentrated by distillation at atmospheric pressure until a temperature of about 82° C. had been reached and admixed with 25 ml of isopropanol. The mixture was inoculated at 70° C. and slowly cooled to room temperature. After cooling to 0° C., the mixture was filtered, the filter cake was washed three times with 30 ml each time of tert-butyl methyl ether/isopropanol (1:1 v/v) and dried at 40° C. under reduced pressure. Yield: 45.8 g (64.4% of theory, corr.) of the compound of the formula (VII-Me), 99.3% by weight, 0.30 area % of isomer (GC), 0.02% by weight of bromide.

Example 12

134.2 g (0.87 mol) of methyl bromoacetate was added dropwise to a solution of 124.1 g (0.94 mol) of ethyldiisopropylamine and 50 g (0.72 mol) of 1,2,3-triazole in 520 ml of ethyl acetate over a period of about 2 hours in such a way that the internal temperature was kept at 35° C. The reaction mixture was subsequently stirred for 2 hours at 35° C., 4 hours at 40° C. and a further 16 hours at 22° C. After cooling to 10° C., the suspension obtained was filtered, the filter cake was washed with 60 ml of ethyl acetate and the combined filtrates were concentrated at 45° C. under reduced pressure. The evaporation residue (123.9 g; 121.9% of theory, uncorrected, max. 0.72 mol) was admixed at 40° C. with 133 g (1.08 mol) of N,N-dimethylformamide dimethyl acetal and stirred at from 76 to 88° C. for 2 hours. Low boilers formed were distilled off during this. The mixture was subsequently cooled to 50° C., 400 ml of acetone were added, undissolved constituents were filtered off hot and washed four times with 25 ml each time of acetone. The combined filtrates were concentrated by distillation, admixed with 150 ml of isopropanol, once again concentrated by distillation at atmospheric pressure until a temperature of about 82° C. had been reached and admixed with 50 ml of isopropanol. At 70° C., the mixture was inoculated and slowly cooled to room temperature. After cooling to 0° C., the mixture was filtered, the filter cake was washed three times with 60 ml each time of tert-butyl methyl ether/isopropanol (1:1 v/v) and dried at 40° C. under reduced pressure. Yield: 88.8 g (62.8% of theory, corr.) of the compound of the formula (VII-Me), 99.9% by weight, 0.30 area % of isomer (GC), 0.1% by weight of bromide.

Example 13

671 g (4.3 mol) of methyl bromoacetate were added dropwise to a solution of 1231 ml (7.2 mol) of ethyldiisopropylamine and 250 g (3.6 mol) of 1,2,3-triazole in 2.6 l of ethyl acetate over a period of about 2 hours in such a way that the internal temperature was kept at 35° C. The reaction mixture was subsequently stirred for 6 hours at 40° C. and a further 16 hours at 22° C. After cooling to 10° C., the suspension obtained was filtered, the filter cake was washed with 1 l of ethyl acetate and the combined filtrates were concentrated at 45° C. under reduced pressure. 123.3 g (max. 0.72 mol) of the evaporation residue (616 g; 121% of theory, uncorrected, max. 3.6 mol) were admixed at 40° C. with 133 g (1.08 mol) of N,N-dimethylformamide dimethyl acetal and stirred at about 80° C. for 2 hours. Low boilers formed were distilled off during this. The mixture was subsequently cooled to 50° C., 400 ml of acetone were added, undissolved constituents were filtered off hot and washed four times with 25 ml each time of acetone. The combined filtrates were concentrated by distillation, admixed with 150 ml of isopropanol, once again concentrated by distillation at atmospheric pressure until a temperature of about 82° C. had been reached and admixed with 50 ml of isopropanol. At 70° C., the mixture was inoculated and slowly cooled to room temperature. After cooling to 0° C., the mixture was filtered, the filter cake was washed three times with 60 ml each time of tert-butyl methyl ether/isopropanol (1:1 v/v) and dried at 40° C. under reduced pressure. Yield: 98.4 g (68.4% of theory, corr.) of the compound of the formula (VII-Me), 98.2% by weight, 0.29 area % of isomer (GC), 0.2% by weight of bromide.

Example 14

The procedure of Example 13 was repeated using only 115 g (0.94 mol; 1.3 equivalents) of dimethylformamide dimethyl acetal. Yield: 91.4 g (64.1% of theory) of the compound of the formula (VII-Me), 99.1% by weight, 0.24 area % of isomer.

Example 15

The procedure of Example 13 was repeated using only 1.3 equivalents of ethyldiisopropylamine (instead of 2 equiv.). Yield: 88.8 g (62.8% of theory) of the compound of the formula (VII-Me), 99.9% by weight, 0.30 area % of isomer.

Example 16

The procedure of Example 13 was repeated, but 400 ml tetrahydrofuran (instead of acetone) were added at 50° C. after the reaction with dimethylformamide dimethyl acetal, undissolved constituents were filtered off hot and washed four times with 25 ml of tetrahydrofuran. The combined filtrates were concentrated by distillation (about 350 ml of distillate were taken off), cooled to RT and stirred for 16 hours. After cooling to 0° C., the mixture was filtered, the filter cake was washed three times with about 40 ml each time of cold tetrahydrofuran and dried at 40° C. under reduced pressure. Yield: 86.8 g (61.4% of theory) of the compound of the formula (VII-Me), 99.8% by weight, 0.30 area % of isomer.

Example 17

The procedure of Example 13 was repeated; after addition of the 400 ml of acetone, undissolved constituents were likewise filtered off hot and washed four times with 25 ml of acetone. However, about 400 ml of acetone were then distilled off at atmospheric pressure and the mixture was slowly cooled to 0° C. The suspension obtained was filtered, the filter cake was washed 3 times with about 40 ml each time of cold acetone and dried at 40° C. under reduced pressure. Yield: 81.0 g (57.3% of theory) of the compound of the formula (VII-Me), 99.8% by weight, 0.30 area % of isomer.

Example 18

67.1 g (0.43 mol) of methyl bromoacetate were added dropwise to a solution of 93.6 g (0.72 mol) of ethyldiisopropylamine and 25 g (0.36 mol) of 1,2,3-triazole in 260 ml of ethyl acetate over a period of about 2 hours in such a way that the internal temperature was kept at 35° C. The reaction mixture was subsequently stirred for 6 hours at 40° C. and a further 16 hours at 22° C. and then cooled to 5° C. The suspension obtained was filtered, the filter cake was washed with 100 ml of ethyl acetate and the combined filtrates were concentrated to half the volume by distillation at atmospheric pressure. The concentrate (198 ml; max. 0.36 mol) was admixed at 45° C. with 88.9 g (0.72 mol) of N,N-dimethylformamide dimethyl acetal and stirred under reflux (from 74 to 82° C.) for 4 hours. After cooling, the suspension obtained was filtered at 60° C., the filter residue was washed twice with 25 ml each time of warm ethyl acetate. The combined filtrates were concentrated by distillation to an internal temperature of 80° C., admixed with 75 ml of isopropanol, once again concentrated by distillation at atmospheric pressure until a temperature of about 82° C. had been reached and admixed with 25 ml of isopropanol. At 70° C., the mixture was inoculated and slowly cooled to room temperature. After cooling to 0° C., the mixture was filtered, the filter cake was washed three times with 30 ml each time of cold isopropanol and dried at 40° C. under reduced pressure. Yield: 48.9 g (67.5% of theory, corr.) of the compound of the formula (VII-Me), 98.0% by weight, 99.7 area %, 0.20 area % of isomer (GC), <0.1% by weight of bromide.

Synthesis of ethyl (2E/Z)-3-(dimethylamino)-2-(1H-1,2,3-triazol-1-yl)acrylate (VII-Et)

Example 19

93.6 g (0.72 mol) of ethyldiisopropylamine were dissolved in 260 ml of ethyl acetate and admixed with 25.0 g (0.36 mol) of 1H-1,2,3-triazole. The solution obtained was heated to 35° C. and 74.8 g (0.43 mol) of ethyl bromoacetate were slowly added over a period of about 90 minutes. The temperature was maintained at 35° C. for a further 2 hours, and the mixture was then stirred for 4 hours at 40° C. and subsequently for 16 hours at about 22° C. The suspension was cooled to 10° C., ethyldiisopropylamine hydrobromide was filtered off and washed three times with 40 ml each time of ethyl acetate. The isomer ratio was 7.5:1 (GC, compound of the formula (V-Et): compound of the formula (VI-Et). The combined filtrates were concentrated at about 45° C. under reduced pressure to about 71 g of a mobile oil, admixed with 79.9 g (0.54 mol) of N,N-dimethylformamide diethyl acetal and stirred at from 88 to 95° C. for 2 hours, with low boilers formed being distilled off. After cooling to about 50° C., 200 ml of acetone were added, the mixture was stirred at 50° C. for about 30 minutes and filtered hot to remove undissolved constituents. The solid which remained was washed four times with 12.5 ml each time of hot acetone. The combined filtrates were concentrated by distillation, admixed with 75 ml of isopropanol and once again heated to boiling. Further low boilers were distilled off until an internal temperature of about 83° C. had been reached. 25 ml of isopropanol were added and the mixture was slowly cooled to 20° C., later to 0° C. No crystallization was observed. After evaporation under reduced pressure, the residue was dissolved hot in 125 ml of methyl tert-butyl ether/isopropanol (3:1 v/v) and once again slowly cooled to 20° C. A small amount of crystals were formed (1.5 g after filtration and drying, no product). The motherliquor was concentrated again and a crystal suspension could be obtained by treatment with 200 ml of methyl tert-butyl ether and 50 ml of isopropanol. The product was isolated by filtration, washed three times with 100 ml each time of methyl tert-butyl ether/isopropanol (9:1 v/v) and dried at 40° C. under reduced pressure. Yield: 29.6 g of compound of the formula (VII-Et) (39% of theory), 98.8 area %, 0.7% of isomer, viz. compound the formula (XX-Et).

Synthesis of 1-[6-(morpholin-4-yl)pyrimidin-4-yl]-4-(1H-1,2,3-triazol-1-yl)-1H-pyrazol-5-ol (enol form) or 2-[6-(morpholin-4-yl)pyrimidin-4-yl]-4-(1H-1,2,3-triazol-1-yl)-1,2-dihydro-3H-pyrazol-3-one (keto form) (I)

Example 20

In a stirred vessel, 42.0 kg (215.1 mol) of 4-(6-hydrazinopyrimidin-4-yl)morpholine and 44.0 kg (224.2 mol) of methyl (2E/Z)-3-(dimethylamino)-2-(1H-1,2,3-triazol-1-yl) acrylate were suspended in 378 kg of ethyl acetate, admixed with 12.1 kg (106.1 mol) of trifluoroacetic acid and heated under reflux (from 78 to 81° C.) at a jacket temperature of 90° C. for 26 hours. The suspension obtained was cooled to 0° C., stirred at 0° C. for 1 hour and filtered. The filter cake was washed with 53 kg of ethyl acetate and dried under reduced pressure at up to 45° C. The filter cake was admixed with a mixture of 355 kg water and 11.7 kg of acetic acid, suspended and stirred at from 50 to 54° C. for 1 hour. After cooling to 24° C., the suspension was filtered. The filter cake was washed firstly with 90 kg of water, then twice with 50 kg each time of methanol and finally dried at from 35 to 45° C. under reduced pressure. Yield: 57.4 kg (84.9% of theory) of the compound of the formula (I), 99.9 area %.

MS (ESI+): m/e=315.0 [M+H]$^+$;

$^1$H NMR (500, 13 MHz, d$_6$-DMSO): 8.55 ppm (s, 1H), 8.38 ppm (d, 1H, 0.6 Hz), 8.27 ppm (s, 1H), 7.86 ppm (d, 1H, 0.6 Hz), 7.42 ppm (s, 1H), 3.71 ppm (s, 8H)

Example 21

10.0 g (51.2 mmol) of 4-(6-hydrazinopyrimidin-4-yl) morpholine and 10.15 g (51.2 mmol) of methyl 3-(dimethylamino)-2-(1H-1,2,3-triazol-1-yl)acrylate were suspended in 100 ml of ethyl acetate, admixed with 2.92 g (25.6 mmol) of trifluoroacetic acid and heated under reflux for 24 hours. The suspension obtained was cooled to 0° C. and filtered. The filter cake was washed twice with 4 ml each time of ethyl acetate and sucked dry well. The filter cake was suspended in 100 ml of water, acidified with 2.4 ml of acetic acid and stirred at 50° C. for about 30 minutes. After cooling to 20° C., the suspension was filtered, the filter cake was washed twice with 10 ml each time of water and dried at 40° C. Yield: 13.5 g (83.9% of theory) of the compound of the formula (I), 99.9 area %, 100% by weight.

Example 22

10.0 g (51.2 mmol) of 4-(6-hydrazinopyrimidin-4-yl) morpholine and 12.2 g (61.5 mmol) of methyl 3-(dimethylamino)-2-(1H-1,2,3-triazol-1-yl)acrylate were suspended in 100 ml of ethyl acetate, admixed with 2.92 g (25.6 mmol) of trifluoroacetic acid and heated under reflux for 24 hours. The suspension obtained was cooled to 0° C. and filtered. The filter cake was washed twice with 4 ml each time of ethyl acetate and sucked dry well. The filter cake was suspended in 100 ml of water, admixed with 2.4 ml of acetic acid and stirred at 50° C. for about 30 min. After cooling to 20° C. the suspension was filtered, the filter cake was washed twice with 10 ml each time of water and dried at 40° C. under reduced pressure. Yield: 14.4 g (85.8% of theory) of the compound of the formula (I), 99.8 area %, 95.9% by weight.

Example 23

10.0 g (51.2 mmol) of 4-(6-hydrazinopyrimidin-4-yl) morpholine and 10.7 g (53.8 mmol) of methyl 3-(dimethylamino)-2-(1H-1,2,3-triazol-1-yl)acrylate were suspended in 100 ml of n-butyl acetate, admixed with 2.92 g (25.6 mmol) of trifluoroacetic acid and stirred under reflux (about 120° C.) for 6 hours. The suspension obtained was stirred for 16 hours at 20° C. and then for 1 hours at 0° C. and filtered. The filter cake was washed twice with 4 ml each time of cold ethyl acetate and dried at 40° C. under reduced pressure. The dried filter cake (15.6 g) was suspended in 100 ml of water, admixed with 2.4 ml of acetic acid and stirred at 50° C. for 30 minutes. After cooling to 20° C., the suspension was filtered, the filter cake was washed twice with 10 ml each time of water and dried at 40° C. under reduced pressure. Yield: 13.9 g (86.3% of theory) of the compound of the formula (I), 99.7 area %, 99.0% by weight.

Example 24

10.0 g (51.2 mmol) of 4-(6-hydrazinopyrimidin-4-yl) morpholine and 10.66 g (53.8 mmol) of methyl 3-(dimethylamino)-2-(1H-1,2,3-triazol-1-yl)acrylate were suspended in 100 ml of n-butanol, admixed with 2.92 g (25.6 mmol) of trifluoroacetic acid and stirred at about 117° C. for 8 hours. The suspension obtained was cooled to 0° C. and filtered. The filter cake was washed twice with 4 ml each time of n-butanol, dried at 40° C. under reduced pressure, subsequently suspended in 100 ml of water, admixed with 2.4 ml of acetic acid and stirred at 50° C. for about 30 minutes. After cooling to 20° C., the suspension was filtered, the filter cake was washed twice with 10 ml each time of water and dried at 40° C. Yield: 13.2 g (81.7% of theory) of the compound of the formula (I), 99.7 area %, 99.0% by weight.

Example 25

10.0 g (51.2 mmol) of 4-(6-hydrazinopyrimidin-4-yl) morpholine and 10.7 g (53.8 mmol) of methyl 3-(dimethylamino)-2-(1H-1,2,3-triazol-1-yl)acrylate were suspended in 100 ml of ethyl acetate, admixed with 7.01 g (61.5 mmol) of trifluoroacetic acid and heated under reflux for 2 hours. 11.4 g (112.7 mmol) of triethylamine were subsequently added and the mixture was stirred under reflux for a further 4 hours. The suspension obtained was cooled to 0° C., stirred at 0° C. for 1 hour and filtered. The filter cake was washed twice with 4 ml each time of ethyl acetate and sucked dry well. The filter cake was suspended in 100 ml of water, acidified to pH 5 with 3.5 ml of acetic acid and stirred at 50° C. for about 30 min. After cooling to 20° C., the suspension was filtered, the filter cake was washed twice with 10 ml each time of water and dried at 40° C. under reduced pressure. Yield: 13.5 g (83.9% of theory) of the compound of the formula (I), 99.8 by area %.

Synthesis of sodium 1-[6-(morpholin-4-yl)pyrimidin-4-yl]-4-(1H-1,2,3-triazol-1-yl)-1H-pyrazol-5-olate (II)

Example 26

In a stirred vessel, 55 kg (175.0 mol) of the compound of the formula (I) were suspended in a mixture of 200 kg of methanol and 30 kg of water, admixed with 17.8 kg (175.9 mmol) of triethylamine, heated to 60° C., stirred further for about 1 hour and filtered hot to separate off undissolved constituents. The filter cake was washed with 15 kg of methanol (60° C.). 18.7 kg (210.4 mmol) of 45% strength sodium hydroxide solution were slowly introduced at 60° C. and 5 kg of methanol were added. 0.12 kg of sodium 1-[6-(morpholin-4-yl)pyrimidin-4-yl]-4-(1H-1,2,3-triazol-1-yl)-1H-pyrazol-5-olate were added as seed crystals, the mixture was stirred at 60° C. for another 1 hour and cooled to 24° C. over a period of about 2 hours. The mixture was stirred for 8 hour at this temperature, subsequently cooled to 0° C. over a period of about 1 hour and filtered in portions by means of a centrifuge. The filter cake was all washed with a mixture of 24 kg of water and 168 kg of methanol and also in each case about 23 kg of methanol and dried altogether at 40° C. under reduced pressure in a dryer for 8 hours. Yield: 57.6 kg (97.9% of theory) of the compound of the formula (II); 100% by weight, 99.9 area %.

$^1$H NMR (500, 13 MHz, d$_6$-DMSO): 8.98 ppm (d, 1H, 1.4 Hz), 8.72 ppm (s, 1H), 8.68 ppm (s, 1H), 8.64 ppm (d, 1H, 1.4 Hz), 7.77 ppm (s, 1H), 4.00-4.25 ppm (m, 8H).

Example 27

12.4 g (39.5 mmol) of the compound of the formula (I) were suspended in a mixture of 63 ml of methanol and 7 ml of water, admixed with 4.0 g (39.6 mmol) of triethylamine and heated to 60° C. 4.2 g (47.4 mmol) of 45% strength sodium hydroxide solution were slowly added at 60° C. After addition of seed crystals, the mixture was cooled to 50° C., stirred at this temperature for 1 hour and subsequently slowly cooled to about 5° C. The suspension obtained was filtered, the filter cake was washed twice with about 4 ml each time of methanol/water (9:1 v/v) and dried at 40° C. for 16 hours under reduced pressure. Yield: 13.1 g (98.7% of theory) of the compound of the formula (II); 100% by weight, 99.9 area %.

Example 28

12.4 g (39.5 mmol) of the compound of the formula (I) were suspended in a mixture of 63 ml of methanol and 7 ml of water, admixed with 4.0 g (39.6 mmol) of triethylamine and heated to 60° C. The solution obtained in this way was added to a solution of 1.9 g (47.4 mmol) of sodium hydroxide in 50 ml of methanol at 60° C. over a period of about 30 minutes. After addition of seed crystals, the mixture was cooled to 50° C., stirred at this temperature for 1 hour and subsequently slowly cooled to about 5° C. The suspension obtained was filtered, the filter cake was washed twice with about 10 ml each time of methanol/water (9:1 v/v) and dried at 40° C. under reduced pressure for 18 hours. Yield: 12.7 g (95.4% of theory) of the compound of the formula (II); 100% by weight, 99.9 area %.

Example 29

12.4 g (39.5 mmol) of the compound of the formula (I) were suspended in a mixture of 63 ml of methanol and 7 ml of water, admixed with 4.0 g (39.6 mmol) of triethylamine and heated to 60° C. The solution obtained in this way was added to 8.5 g (47.4 mmol) of methanolic sodium methoxide solution (30% strength) in 50 ml of methanol at 60° C. over a period of about 30 minutes. After addition of seed crystals, the mixture was cooled to 50° C., stirred at this temperature for 1 hour and subsequently slowly cooled to about 5° C. The suspension obtained was filtered, the filter cake was washed twice with about 4 ml each time of methanol/water (9:1 v/v) and dried at 40° C. under reduced pressure for 16 hours. Yield: 12.8 g (96.5% of theory) of the compound of the formula (II); 100% by weight, 99.9 area %.

The invention claimed is:

1. A process for preparing 1-[6-(morpholin-4-yl)pyrimidin-4-yl]-4-(1H-1,2,3-triazol-1-yl)-1H-pyrazol-5-ol (I—enol form) or 2-[6-(morpholin-4-yl)pyrimidin-4-yl]-4-(1H-1,2,3-triazol-1-yl)-1,2-dihydro-3H-pyrazol-3-one (I—keto form), corresponding to the formula (I)

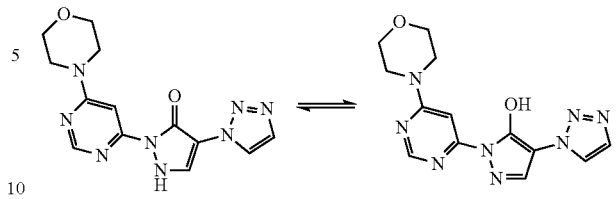

(I)

comprising
a) reacting 1,2,3-triazole (III) with methyl bromoacetate (IV-Me-Br) or ethyl bromoacetate (IV-Et-Br) in the presence of ethyldiisopropylamine as base in a solvent in the temperature range from 20 to 80° C. to form compounds of the formulae (V-Me) and (VI-Me),

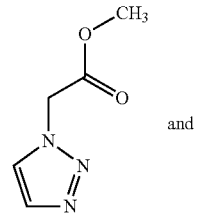

(V-Me)

and

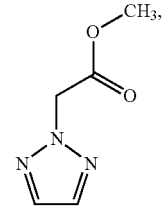

(VI-Me)

or compounds of the formulae (V-Et) and (VI-Et)

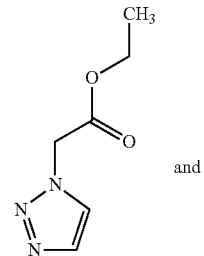

(V-Et)

and

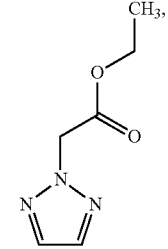

(VI-Et)

b) reacting the compounds of the formulae (V-Me) and (VI-Me) or the compounds of the formulae (V-Et) and (VI-Et), which are present in a ratio of at least 6:1 to one another, with dimethylformamide dimethyl acetal (XIX-Me) or dimethylformamide diethyl acetal (XIX-Et) in an inert solvent, and subsequently crystallizing by cooling the solution or by distilling off the solvent and adding a second solvent to form methyl (2E/Z)-3-(dimethylamino)-2-(1H-1,2,3-triazol-1-yl)acrylate (VII-Me) or ethyl (2E/Z)-3-(dimethylamino)-2-(1H-1,2,3-triazol-1-yl)acrylate (VII-Et), and c) reacting the methyl (2E/Z)-3-(dimethylamino)-2-(1H-1,2,3-triazol-1-yl)acrylate (VII-Me) or the ethyl (2E/Z)-3-(dimethylamino)-2-(1H-1,2,3-triazol-1-yl)acrylate (VII-Et) with 4-(6-hydrazinopyrimidin-4-yl)morpholine (XI) in the presence of trifluoroacetic acid in an inert solvent, wherein the compound of formula (I) is prepared.

2. The process according to claim 1, further comprising the step of purifying the compound of formula (I) with water and an acid at a pH of from 4 to 5.5.

3. The process according to claim 1, further comprising reacting the compound of the formula (I) in a subsequent step with sodium hydroxide or aqueous sodium hydroxide solution or sodium methoxide or sodium ethoxide or a sodium salt to form sodium 1-[6-(morpholin-4-yl)pyrimidin-4-yl]-4-(1H-1,2,3-triazol-1-yl)-1H-pyrazol-5-olate (II).

4. The process according to claim 1, wherein the 4-(6-hydrazinopyrimidin-4-yl)morpholine (XI) is prepared by reacting 4,6-dichloropyrimidine (VIII) with hydrazine hydrate (XII hydrate) in a solvent, optionally in the presence of an auxiliary base, and heating the resulting reaction mixture without isolation of the resulting 4-chloro-6-hydrazinopyrimidine (XV) in a second stage after addition of morpholine (IX) and a further auxiliary base and subsequently isolating the compound of the formula (XI)

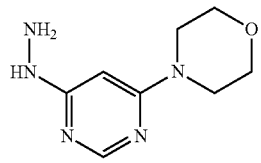

(XI)

after crystallization.

5. The process according to claim 4, wherein the auxiliary base in the first step is triethylamine or ethyldiisopropylamine.

6. The process according to claim 4, wherein the reaction is carried out using sodium hydrogencarbonate, potassium hydrogencarbonate, sodium hydroxide or potassium hydroxide as a further auxiliary base.

7. The process according to claim 1, wherein methyl (2E/Z)-3-(dimethylamino)-2-(1H-1,2,3-triazol-1-yl)acrylate (VII-Me) or ethyl (2E/Z)-3-(dimethylamino)-2-(1H-1,2,3-triazol-1-yl)acrylate (VII-Et) is prepared by reacting the compounds of the formulae (V-Me) and (VI-Me) or the compounds of the formulae (V-Et) and (VI-Et), which are present in a ratio of at least 6:1 to one another, with dimethylformamide dimethyl acetal (XIX-Me) or dimethylformamide diethyl acetal (XIX-Et) in an inert solvent and subsequently crystallizing the product by cooling the solution or by distilling off the solvent and adding a second solvent.

8. The process according to claim 7, wherein compounds of the formulae (V-Me) and (VI-Me) or compounds of the formulae (V-Et) and (VI-Et) are prepared by reacting 1,2,3-triazole (III) with methyl bromoacetate (IV-Me-Br) or ethyl bromoacetate (IV-Et-Br) in the presence of ethyldiisopropylamine as base in a solvent in the temperature range from 20 to 80° C.

\* \* \* \* \*